(12) United States Patent
Ma et al.

(10) Patent No.: US 8,445,588 B2
(45) Date of Patent: May 21, 2013

(54) HYDROPHILIC COPOLYMERS AND ASSEMBLIES CONTAINING THE SAME

(75) Inventors: Peter X. Ma, Ann Arbor, MI (US); Jianxiang Zhang, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 748 days.

(21) Appl. No.: 12/543,381

(22) Filed: Aug. 18, 2009

(65) Prior Publication Data

US 2010/0048734 A1    Feb. 25, 2010

Related U.S. Application Data

(60) Provisional application No. 61/091,217, filed on Aug. 22, 2008.

(51) Int. Cl.
*C08B 31/00* (2006.01)

(52) U.S. Cl.
USPC ........ 525/54.24; 514/449; 514/453; 527/300; 527/312

(58) Field of Classification Search
USPC ............... 514/449, 453; 525/54.24; 527/300, 527/312
See application file for complete search history.

(56) References Cited

U.S. PATENT DOCUMENTS 7,141,540 B2    11/2006    Wang et al.

OTHER PUBLICATIONS

Harada, A., et al.; Macromolecules, 1995, vol. 28, p. 5294-5299.*
Kanayama, N., et al.; ChemMedChem, 2006, vol. 1, p. 439-444.*

* cited by examiner

*Primary Examiner* — Robert Jones, Jr.
(74) *Attorney, Agent, or Firm* — Dierker & Associates, P.C.

(57) ABSTRACT

A water soluble copolymer includes first and second hydrophilic block segments or graft chains. The first hydrophilic block segment or graft chain contains cyclodextrin groups in at least a majority of its repeating units, and the second hydrophilic block segment or graft chain contains repeating units other than cyclodextrin groups. The first and second block segments or graft chains are covalently linked.

4 Claims, 25 Drawing Sheets

HYDROPHILIC COPOLYMERS AND ASSEMBLIES CONTAINING THE SAME

CROSS-REFERENCE TO RELATED APPLICATIONS

This application claims the benefit of U.S. Provisional Patent Application Ser. No. 61/091,217, filed Aug. 22, 2008, which application is incorporated herein by reference in its entirety.

STATEMENT REGARDING FEDERALLY SPONSORED RESEARCH OR DEVELOPMENT

This invention was made in the course of research supported by grants from the National Institutes of Health (NIH) and the National Institute of Dental and Craniofacial Research (NIDCR), Grant Nos. DE015384 and DE017689, and from the National Institutes of Health (NIH) and the National Institute of General Medical Sciences (NIGMC), Grant No. GM075840. The U.S. government has certain rights in the invention.

BACKGROUND

The present disclosure relates generally to hydrophilic copolymers and assemblies containing the same.

Polymeric assemblies, such as star micelles, cylindrical micelles, wormlike micelles, multi-compartment micelles, toroidal assemblies, vesicles, nanofibers, helical superstructure and macroscopic tubes, have been utilized as carriers for drug and gene delivery. These organized assemblies are suitable for use in a wide variety of applications, such as bioengineering, biomedicine, materials science and pharmaceutics. In some instances, polymeric micelles with a core-shell structure are assembled in an aqueous solution utilizing the hydrophobic interactions between core-forming segments. The hydrophobic inner core serves as a container for hydrophobic drugs, while the outer shell provides micelles with colloidal stability and extends the circulation time in the bloodstream after their systemic administration. The synthesis procedure for conventional micelles of block copolymers with various hydrophobic blocks may be relatively complicated since the loading capability for various drugs is mainly determined by the compatibility between a drug and the hydrophobic segment.

BRIEF DESCRIPTION OF THE DRAWINGS

Features and advantages of embodiments of the present disclosure will become apparent by reference to the following detailed description and drawings, in which:

FIGS. 7A and 7C are emission spectra with an excitation wavelength at 339 nm and FIGS. 7B and 7D are plots of $I_{338}/I_{333}$, $I_3/I_1$ and $I_E/I_M$ as a function of the concentration of PEG-b-PCD or β-CD, where $I_{338}/I_{333}$ is the intensity ratio of the (0, 0) band in pyrene excitation spectrum, $I_3/I_1$ is the intensity ratio between the third and first vibrational bands in pyrene emission spectrum, and $I_E/I_M$ is the intensity ratio of the excimer (475 nm) to monomer (371 nm) in emission spectrum;

FIGS. 21A and 21C illustrate assemblies including PBLA:PEG-b-PCD at a ratio of 1:20 and FIG. 21B illustrates assemblies including PBLA:PEG-b-PCD at a ratio of 8:20;

DETAILED DESCRIPTION

Figure 1:
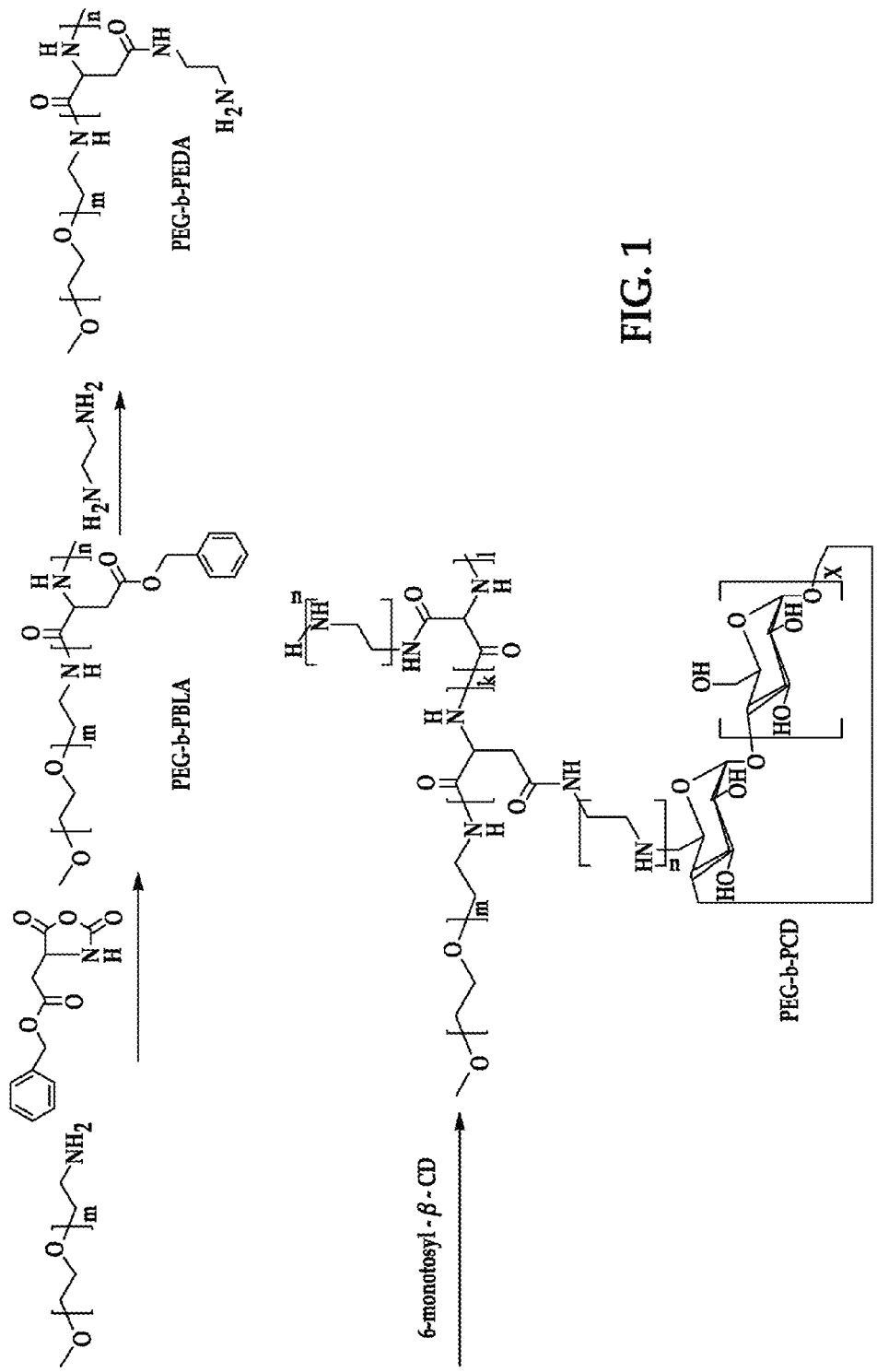
FIG. 1 is a schematic depiction of the synthesis of a diblock hydrophilic copolymer characterized by tandem alignment of a polyethylene glycol block and a polyaspartamide block carrying cyclodextrin groups.

Embodiments of the water soluble copolymer disclosed herein may advantageously be used to fabricate nano and/or micro-sized particles for use in delivery of biologics and other functional molecules. As used herein, "nanoparticles" have a diameter ranging from about $10^{-10}$ meters to about $10^{-6}$ meters; and "microparticles" have a diameter ranging from about $10^{-6}$ meters to about $10^{-3}$ meters.

The cyclodextrin portion of the particles (based on hydrophilic block/graft copolymers disclosed herein and discussed further hereinbelow) may act as a host for a guest hydrophobic molecule or polymer, or hydrophobic unit of a molecule or polymer, via inclusion interaction. The guest molecule or polymer may be small enough such that it associates with a single cyclodextrin group, or may be large enough (such as, for example, a synthetic polymer, oligomer, natural macromolecule, or derivatives thereof) such that it associates with multiple cyclodextrin groups. The nano- or micro-sized particles are advantageously able to serve as delivery vehicles for the guest molecules/polymers or other molecules that associate with the guest molecules/polymers in a variety of biomedical, cosmetic, agricultural, industrial or household applications. Non-limiting examples of the molecules or polymers to be delivered include proteins, peptides, hormones, DNAs, RNAs, siRNAs, therapeutic drugs, nutrients, pigments, fertilizers, fragrances, food additives, and the like. Furthermore, the particles may be used as a substrate to support cell culture or to sort cells, as a selective absorption substrate to concentrate or separate substances (such as small or large molecules including proteins and other natural/synthetic molecules), and/or as image-enhancing agents (such as fluorescence, scattering, or radio-opaque agents) in various imaging applications. Still further, it is believed that the copolymers disclosed herein may be suitable for use in vivo.

It is to be understood that in any of the above-mentioned applications, the nano- and/or micro-sized particles may be used alone or in a media (i.e., liquid formulations, such as tissue culture media) or matrix (i.e., gels or solid materials, such as tissue culture substrates, implants, and tissue engineering scaffolds).

The water soluble block or graft copolymers that make up the particles disclosed herein include at least two distinctly different hydrophilic repeating units. Generally, the first hydrophilic block segment or graft chain contains cyclodextrin groups in at least a majority of its repeating units. Non-limiting examples of such cyclodextrin groups include α-cyclodextrin groups, β-cyclodextrin groups, γ-cyclodextrin groups, and combinations thereof. The second hydrophilic block segment or graft chain contains repeating units other than cyclodextrin groups (i.e., the second hydrophilic block segment or graft chain does not include cyclodextrin groups). The first and second hydrophilic block segments or graft chains are covalently linked to each other. In some instances, the block of the first hydrophilic block segment or graft chain is directly covalently linked to the second hydrophilic block segment or graft chain. In other instances, both the first and second hydrophilic block segments or graft chains are covalently linked as respective side groups on another polymer backbone or compound.

In one example of synthesizing the water soluble block or graft copolymers, a polymer containing two hydrophilic block segments or graft chains is formed initially without cyclodextrin, and then the cyclodextrin groups are covalently linked to one of the hydrophilic block segments or graft chains via nucleophilic reaction. Non-limiting examples of this synthesis are shown in FIGS. 1 and 2A.

Figure 2A:
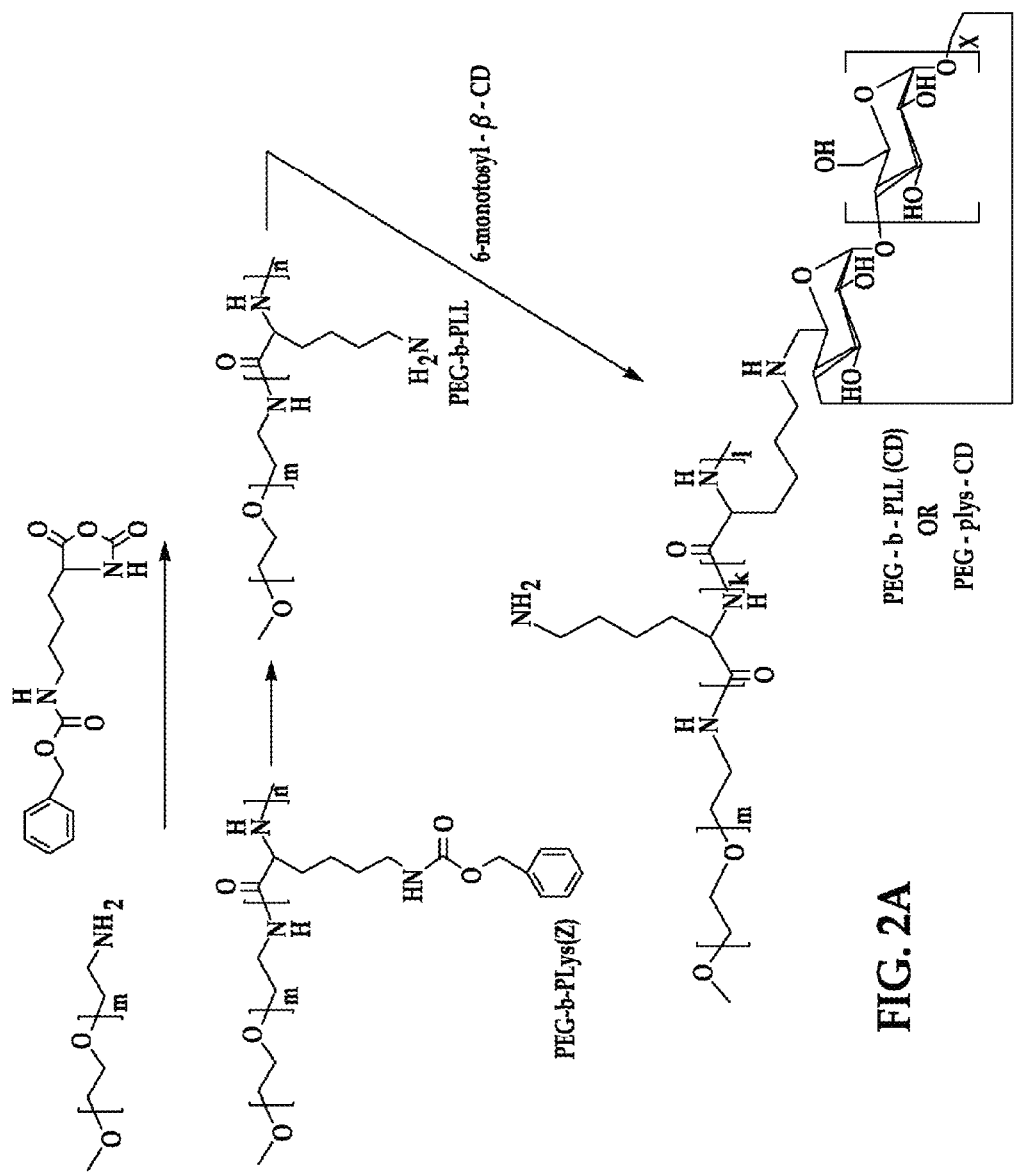
FIG. 2A is a schematic depiction of the synthesis of a diblock hydrophilic copolymer characterized by tandem alignment of polyethylene glycol block and a poly(L-lysine) block carrying cyclodextrin groups.

More specifically, FIG. 1 illustrates the synthesis of PEG-b-PCD (i.e., a polyethylene glycol block and a polyaspartamide block carrying α-, β- or γ-cyclodextrin groups). While a polyethylene glycol block is shown in this example, it is to be understood that the second hydrophilic block/chain may be any hydrophilic polymer block. For example, the second hydrophilic block/chain may be a copolymer of random units or a copolymer of two or more block or graft segments. More particularly, non-limiting examples of the second hydrophilic block/chain include polyvinylpyrrolidone (PVP), poly (N-isopropylacrylamide) (PNIPAm), poly (N,N-dimethylacrylamide) (PDMAm), polyacrylamide (Pam), poly(vinyl alcohol) (PVA), dextrin, celluloses, gelatin, collagen, derivatives thereof, and other synthetic or natural hydrophilic polymers.

In the synthesis of FIG. 1, α-Methoxy-ω-amino-PEG (with an average molecular weight of 5000) may be selected to form the second hydrophilic segment, at least in part because it provides the final assemblies with stealthy characteristics (i.e., the segment forms "shell-like" structure that can stabilize the formed mini particle, thereby substantially or completely preventing aggregation of such particles). In this example, an intermediate polymer, which is a polyaspartamide block containing ethylenediamine (EDA) unit (PEG-b-PEDA), is synthesized first. β-benzyl-L-aspartate N-carboxyanhydride (BLA-NCA) is polymerized by the initiation from the terminal primary amino group of α-methoxy-ω-amino-PEG (MPEG-$NH_2$) to obtain PEG-b-PBLA. The polymerization may take place in dimethylformide (DMF), dimethylsulfoxide (DMSO), dimethylacetamide (DMAc), chloroform, or another like solvent at a temperature ranging from about room temperature to about 80° C. In one example, the polymerization temperature is about 40° C. The PEG-b-PBLA is then reacted with EDA to form PEG-b-PEDA. A cyclodextrin-containing compound (e.g., 6-monotosyl β-cyclodextrin) is added to PEG-b-PEDA in an anhydrous solvent (e.g., dimethyl sulfoxide (DMSO, dimethylformide (DMF), dimethylacetamide (DMAc)) to link the cyclodextrins to the PEDA block. The reaction of the cyclodextrin-containing compound with PEG-b-PEDA results in the cyclodextrin groups (e.g., β-CD) covalently linking to EDA side groups to form PEG-b-PCD (as shown in FIG. 1).

It is believed that the temperature and the reaction time affect the conjugation of the cyclodextrin groups onto the side chains of the PEDA block. A relatively high efficient conjugation (up to about 90%) of the cyclodextrin groups to EDA may be achieved by adding an excess amount of the cyclodextrin-containing compound to the PEG-b-PEDA. In some instances, a desirable temperature is about 70° C., and a desirable reaction time is at least 5 days. In other instances, the desirable temperature ranges from room temperature to about 80° C., and the desirable reaction time ranges from 1 day to 10 days.

The PEG-b-PCD structure formed via the non-limiting example synthesis of FIG. 1 is also shown below:

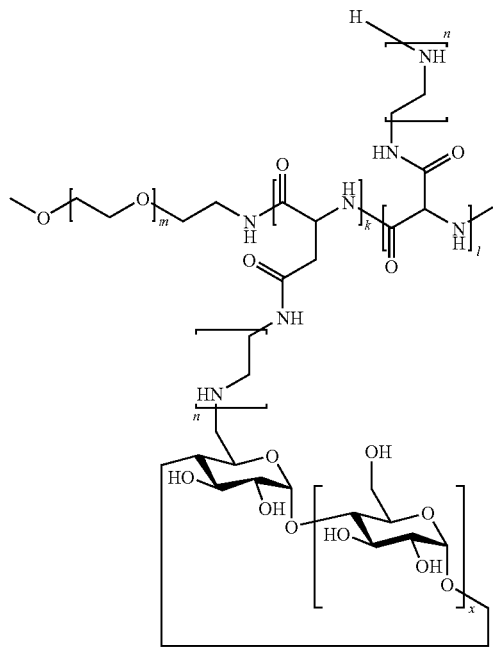

wherein m=5 to 500 or 10 to 250, wherein n=1 to 5, wherein k+l=any desirable length (e.g., 5 to 100) and k≧1≧0, and wherein X=5 when the first hydrophilic block segment is the polyaspartamide block carrying α-cyclodextrin groups, X=6 when the first hydrophilic block segment is the polyaspartamide block carrying β-cyclodextrin groups, or X=7 when the first hydrophilic block segment is the polyaspartamide block carrying γ-cyclodextrin groups.

FIG. 2A illustrates another example of the formation of a copolymer via nucleophilic reaction. More specifically, FIG. 2A illustrates the synthesis of PEG-b-PLL(CD) or PEG-Plys-CD (i.e., a polyethylene glycol-block-poly(L-lysine) conjugated with α-, β- or γ-cyclodextrin groups). While a polyethylene glycol block is shown in this example, it is to be understood that the second hydrophilic block/chain may be any hydrophilic polymer block. For example, the second hydrophilic block/chain may be a homopolymer or a copolymer of random units or a copolymer of two or more block or graft segments.

In this example, the polyethylene glycol-block-poly(L-lysine) copolymer (PEG-b-PLL) is synthesized first. To obtain PEG-b-P(Lys(Z)), ε-(benzyloxycarbonyl)-L-lysine (Lys(Z)-NCA) is polymerized in DMF (or DMSO, DMAc, chloroform, or the like) at 40° C. (or any temperature ranging from room temperature to about 80° C.) by the initiation from the terminal primary amino group of MPEG-NH$_2$. PEG-b-PLL is then obtained by the de-protection of PEG-b-P(Lys(Z)) in, for example, trifluoroacetic acid.

The PEG-b-PLL is lyophilized, and is reacted with an excess amount of a cyclodextrin-containing compound (e.g., 6-monotosyl α-cyclodextrin or 6-monotosyl β-cyclodextrin) in an anhydrous solvent (e.g., dimethyl sulfoxide, DMAc, DMSO, or another suitable anhydrous solvent). As mentioned herein above, the conjugation of the cyclodextrin groups to the poly(L-lysine) block may be manipulated by altering the time and temperature of the reaction. In a non-limiting example, this reaction is allowed to take place for about 5 days at 70° C. The time and temperature for this reaction may range, respectively, from room temperature to about 90° C. and from 1 to 10 days.

The PEG-b-PLL(CD)/PEG-Plys-CD) structure formed via the synthesis of FIG. 2A is also shown below:

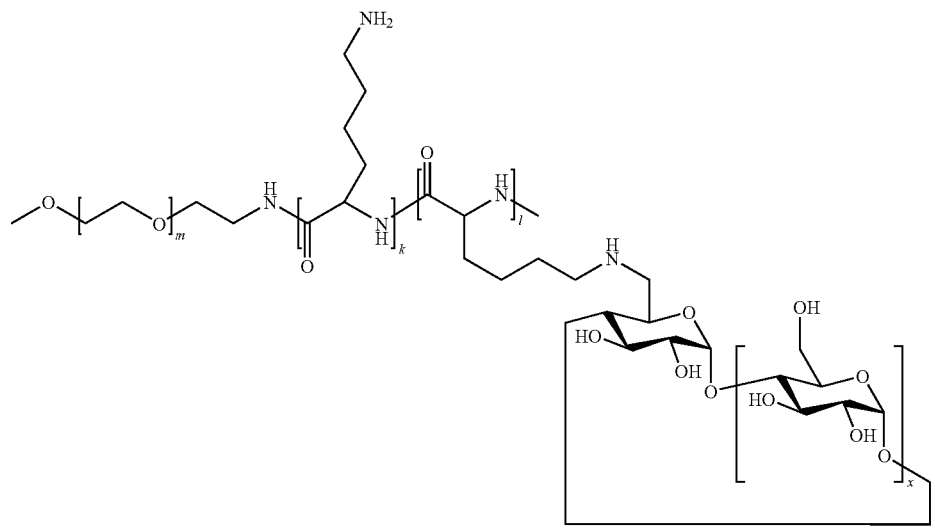

wherein m=5 to 500 or 10 to 250, wherein k+1=any desirable length (e.g., 5 to 100) and 1≧k≧0, and wherein X=5 when the first hydrophilic block segment is the poly(L-lysine) block carrying α-cyclodextrin groups, X=6 when the first hydrophilic block segment is the poly(L-lysine) block carrying β-cyclodextrin groups, or X=7 when the first hydrophilic block segment is the poly(L-lysine) block carrying γ-cyclodextrin groups.

Figure 2B:
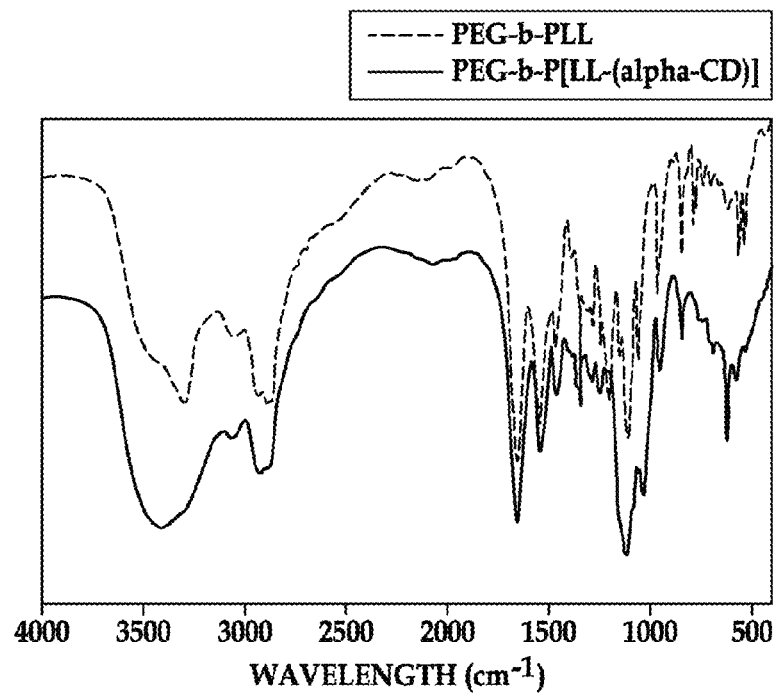
FIGS. 2B and 2C respectively illustrate the FT-IR spectra and $^1$H NMR spectra of at least PEG-b-PLL and PEG-b-PCD [LL-α-CD], the latter of which is an example of the diblock hydrophilic copolymer formed via the synthesis shown in FIG. 2A.
Figure 2C:
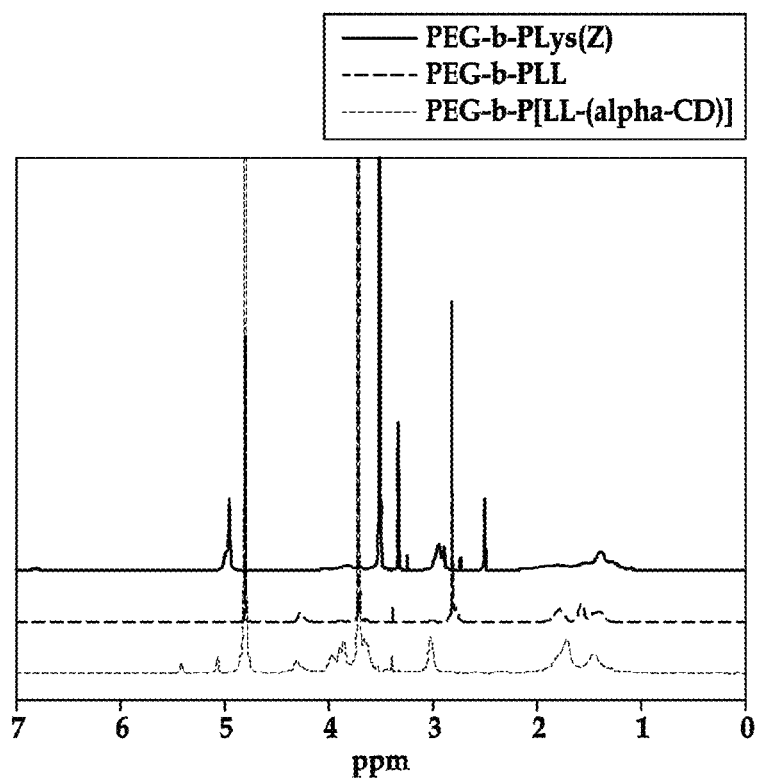

FIGS. 2B and 2C are FT-IR and $^1$H NMR spectra of at least PEG-b-P[LL-(α-CD), which illustrate the successful introduction of α-cyclodextrin groups onto the side chain of PEG-b-PLL.

In the reaction schemes shown in FIGS. 1 and 2A, it is to be understood that the resulting water soluble copolymers (e.g., PEG-b-PCD and PEG-b-PLL(CD)/PEG-Plys-CD) may be dialyzed against sodium hydroxide (NaOH) or deionized water for a predetermined time ranging from about 1 day to about 5 days to remove any unreacted cyclodextrin units. When NaOH is used, after the copolymers are dialyzed against NaOH, the copolymers may also be dialyzed against distilled (or deionized) water. In either instance, the resulting water soluble copolymers may be filtered and lyophilized to obtain a powder. In one embodiment, filtering is accomplished using a 0.22 micron syringe filter, but it is to be understood that any suitable filter may be used.

In another example of synthesizing the water soluble block or graft copolymers, a polymer including the first hydrophilic block segment or graft chain is formed initially, and then the second hydrophilic block segment or graft chain may be covalently linked thereto. In some instances, the first and second hydrophilic graft chains are covalently linked to a side chain of another (i.e., a third) polymer or compound. It is to be understood that the first and second graft chains may be in a random sequence on the third polymer/compound, or they may be in an ordered sequence on the third polymer/compound.

In one non-limiting example, the first and second hydrophilic graft chains are covalently linked to polyethleneimine (PEI). Other suitable polymers to which the first and second chains may be linked include polyvinylpyrrolidone (PVP), poly (N-isopropylacrylamide) (PNIPAm), poly(N,N-dimethylacrylamide) (PDMAm), polyacrylamide (Pam), poly (vinyl alcohol) (PVA), dextrin, celluloses, gelatin, collagen, derivatives thereof, and other synthetic or natural hydrophilic polymers. A non-limiting example of this is shown below.

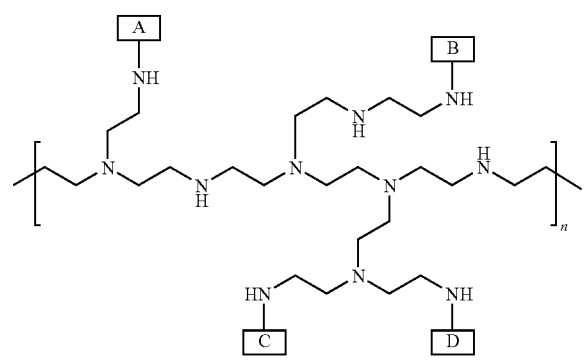

In one example, two of A, B, C and D include the first hydrophilic graft chain with cyclodextrin units and one of A, B, C, and D includes the second hydrophilic graft chain. The other of A, B, C and D may be either the first or the second hydrophilic graft chain. Examples of A, B, C, and/or D include H, PEG, or cyclodextrins. The repeating units in the formula can be the same or different from one another in the polymer chain (see, for example, PEI-CD-PEG in FIG. 3).

Figure 3:
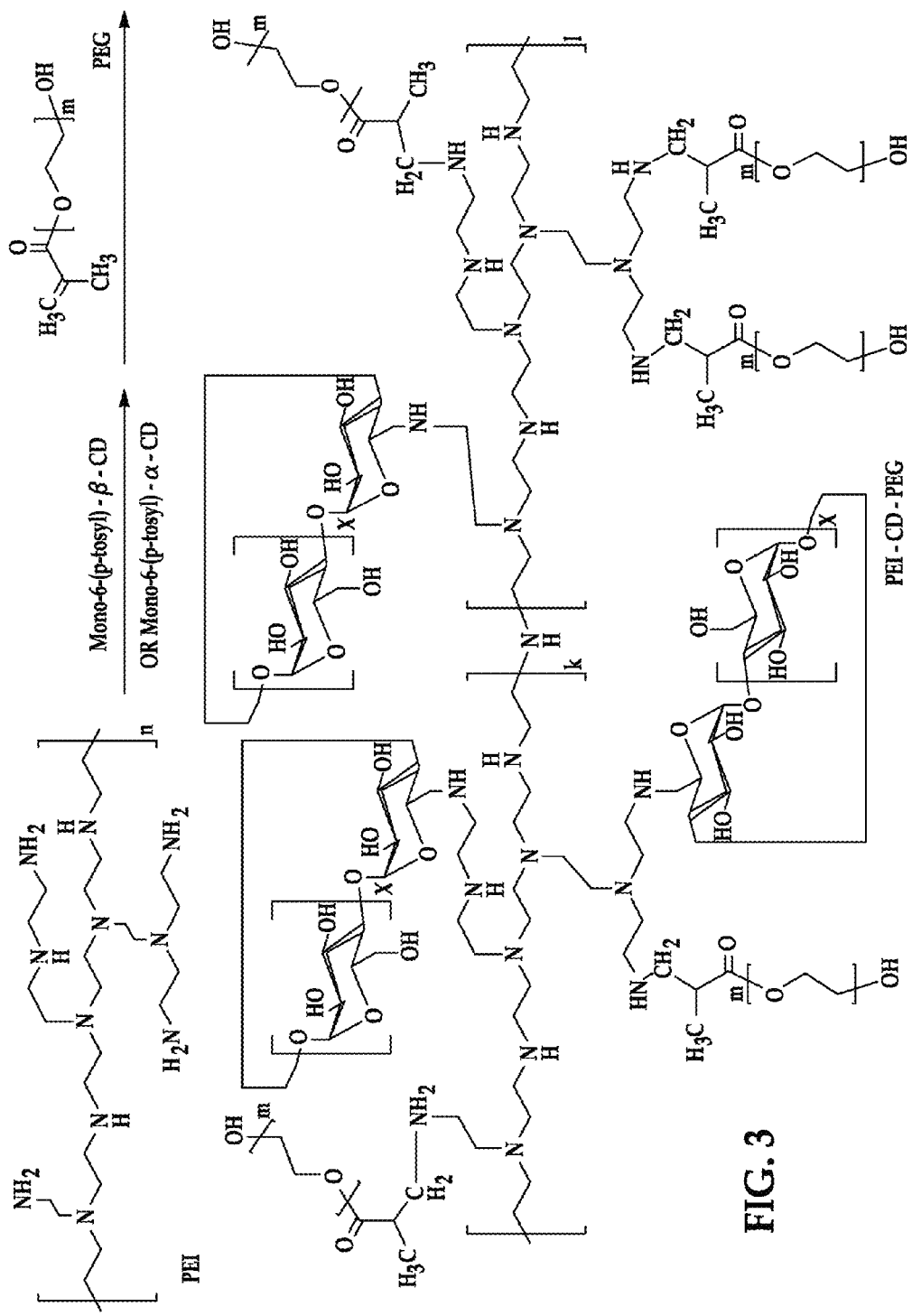
FIG. 3 is a schematic depiction of the synthesis of a cyclodextrin containing graft copolymer based on a branched polyethyleneimine.

A non-limiting example of the synthesis of such a copolymer is shown in FIG. 3. It is to be understood that the resulting copolymer of FIG. 3 is one of many possible combinations of the first and second hydrophilic graft chains on a polymer backbone.

In FIG. 3, the first hydrophilic graft chain includes β-cyclodextrin groups or α-cyclodextrin groups, the second hydrophilic graft chain include PEG, and the third polymer to which the graft chains are covalently linked is polyethleneimine (PEI).

While the structure of the intermediate polymer including the first hydrophilic graft chain and not the second hydrophilic graft chain is not shown in FIG. 3, this intermediate polymer (cyclodextrin conjugated polyethleneimine) is formed by dissolving branched PEI in a solvent (e.g., DMSO), and then adding the cyclodextrin-containing compound (e.g., mono-6-(p-tosyl)-β-CD or α-cyclodextrin groups). A reaction between the branched PEI and the cyclodextrin-containing compound is allowed to occur at a predetermined temperature (e.g., 75° C.) for a predetermined time (e.g., 7 days). The time and temperature for the reaction between the branched PEI and the cyclodextrin-containing compound may range, respectively, from room temperature to about 90° C. and from 1 to 10 days. The resulting intermediate polymer (PEI-CD) may be purified by dialysis.

The second hydrophilic graft chain (e.g., polyethylene glycol) may then be covalently linked to the CD conjugated PEI by reacting, for example, polyethylene glycol methacrylate with the PEI-CD. The resulting copolymer (PEI-CD-PEG) includes a polymeric backbone having the first and second hydrophilic graft chains covalently linked thereto as side chains. The copolymer may be purified by dialysis. One example of the PEI-CD-PEG structure formed via the synthesis of FIG. 3 is also shown below:

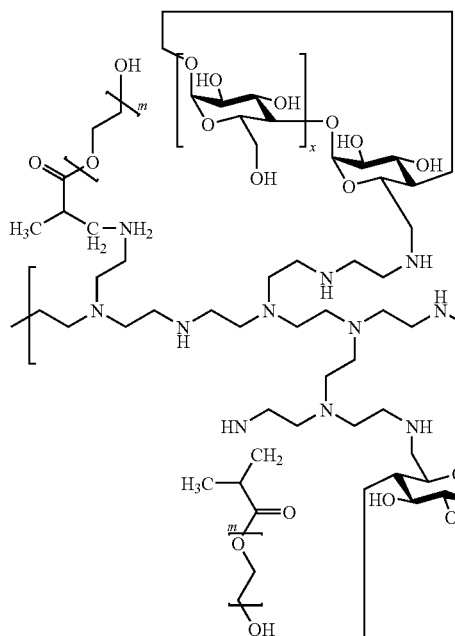
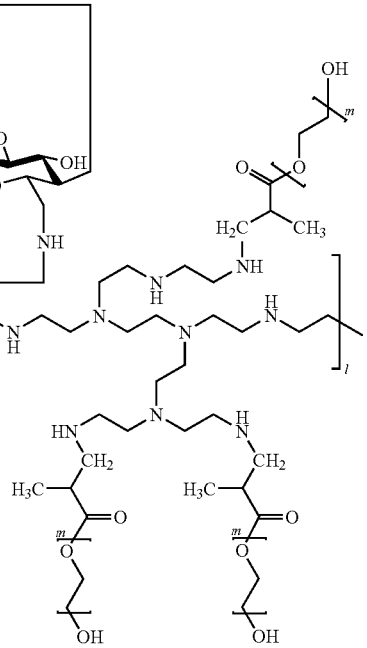

wherein m=5 to 500, k+1=1 to 100, and wherein x=5 when the first hydrophilic graft chain includes α-cyclodextrin groups, x=6 when the first hydrophilic graft chain includes β-cyclodextrin groups, or x=7 when the first hydrophilic graft chain includes γ-cyclodextrin groups.

In still another example of synthesizing the water soluble block or graft copolymers, click chemistry may be used to introduce the cyclodextrin units to the second hydrophilic block segment. An intermediate polymer is formed and is used in a catalyzed azide-alkyne cycloaddition reaction to link the cyclodextrin units thereto.

Figure 4A:
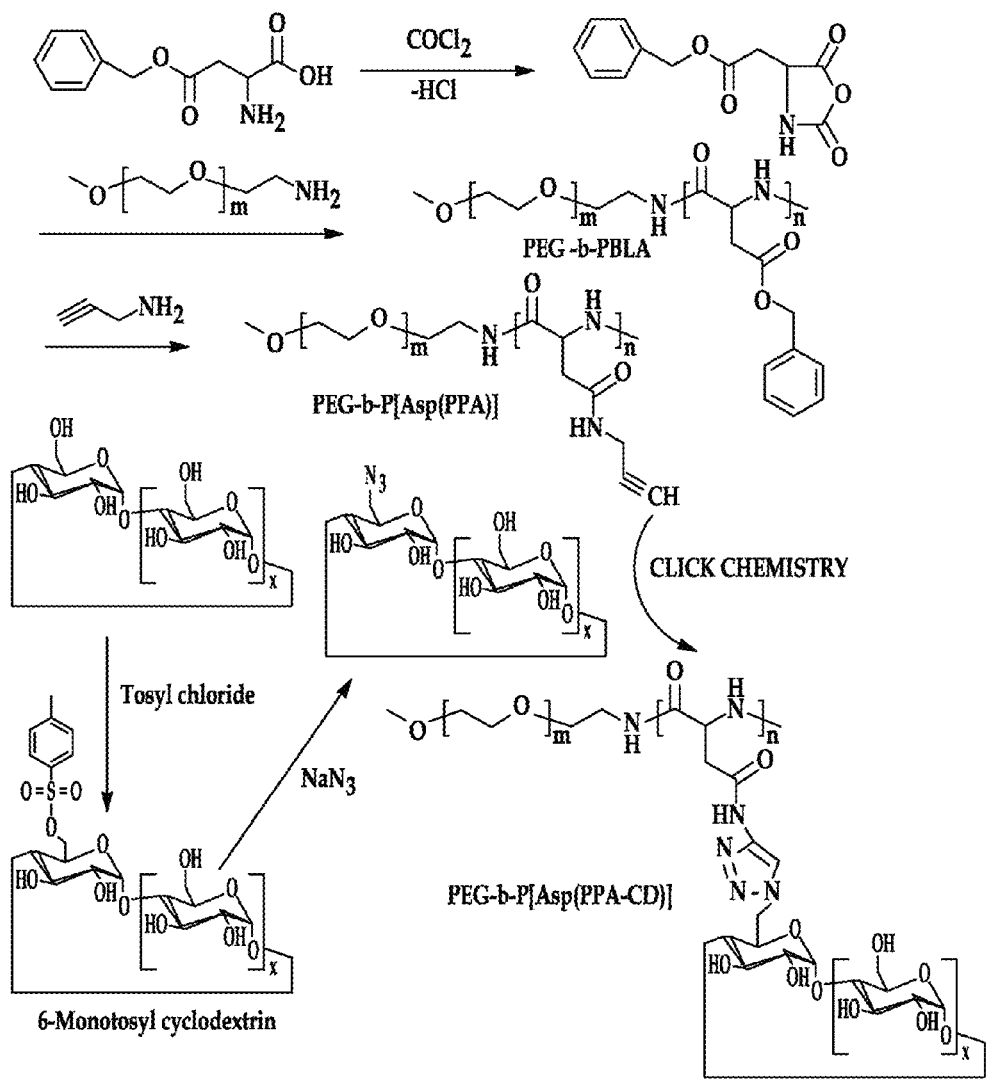
FIG. 4A is a schematic depiction of the synthesis of a block hydrophilic copolymer characterized by tandem alignment of a polyethylene glycol block and a block carrying cyclodextrin groups based on a propargylamine containing copolymer via a "click chemistry" approach.

An example of this reaction scheme is shown in FIG. 4A. In this particular example, β-benzyl-L-aspartate N-carboxyanhydride (BLA-NCA) is initially formed via the reaction of a related amino acid with triphosgene. The BLA-NCA is then polymerized in dimethylformide (or DMSO, DMAc, chloroform, or the like) at about 40° C. (or any desirable temperature ranging from room temperature to about 80° C.) by the initiation from the terminal primary amino group of α-methoxy-ω-amino-PEG (MPEG-NH$_2$) to obtain PEG-b-PBLA.

The intermediate polymer, PEG-b-P[Asp(PPA)], may be prepared through the quantitative aminolysis reaction of PEG-b-PBLA in dry DMSO (or DMSO, DMAc, chloroform, or the like) at 40° C. (or any desirable temperature ranging from room temperature to about 80° C.) in the presence of an excess (e.g., 5-fold molar) of propargylamine. After a predetermined time, the reaction mixture is dialyzed against deionized water (MWCO: 3500), and the final aqueous solution is lyophilized to a white powder. In an example embodiment, the predetermined time for the aminolysis reaction is at least about 48 hours. In another example, the aminolysis reaction time ranges from about 1 hour to 1 day, or up to 3 days.

PEG-b-P[Asp(PPA-CD)] is then synthesized using a Cu(I)-catalyzed azide-alkyne cycloaddition reaction. The Cu(I)-catalyzed azide-alkyne cycloaddition reaction takes place between PEG-b-P[Asp(PPA)] and mono-6-azido β-CD (or another α-cyclodextrin or γ-cyclodextrin) in DMSO (or DMSO or DMAc). As shown in FIG. 4A, mono-6-azido β-CD may be formed from i) the reaction of β-cyclodextrin with tosyl chloride, which yields 6-monotosyl-β-CD, and then ii) the reaction of 6-monotosyl-β-CD with sodium azide (NaN$_3$). In one embodiment, a mixture of sodium ascorbate and copper(II) sulfate pentahydrate may be employed as the catalyzer in the azide-alkyne cycloaddition reaction.

Figure 4B:
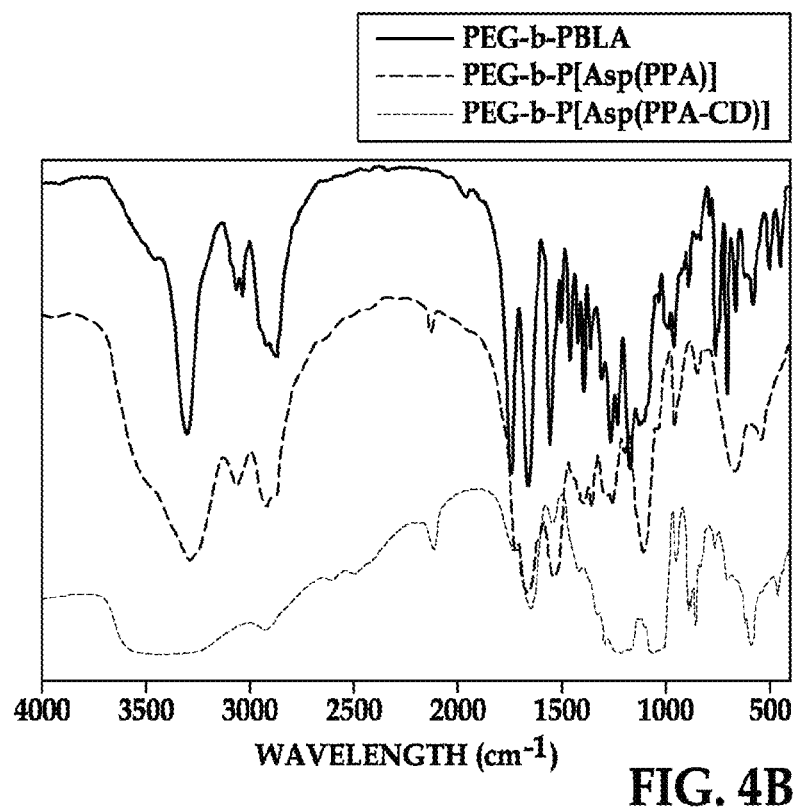
FIGS. 4B and 4C respectively illustrate the FT-IR spectra and $^1$H NMR spectra of PEG-b-PBLA, PEG-b-P[Asp(PPA)] and PEG-b-P[PPA-CD], each of which is formed during the synthesis shown in FIG. 4A.
Figure 4C:
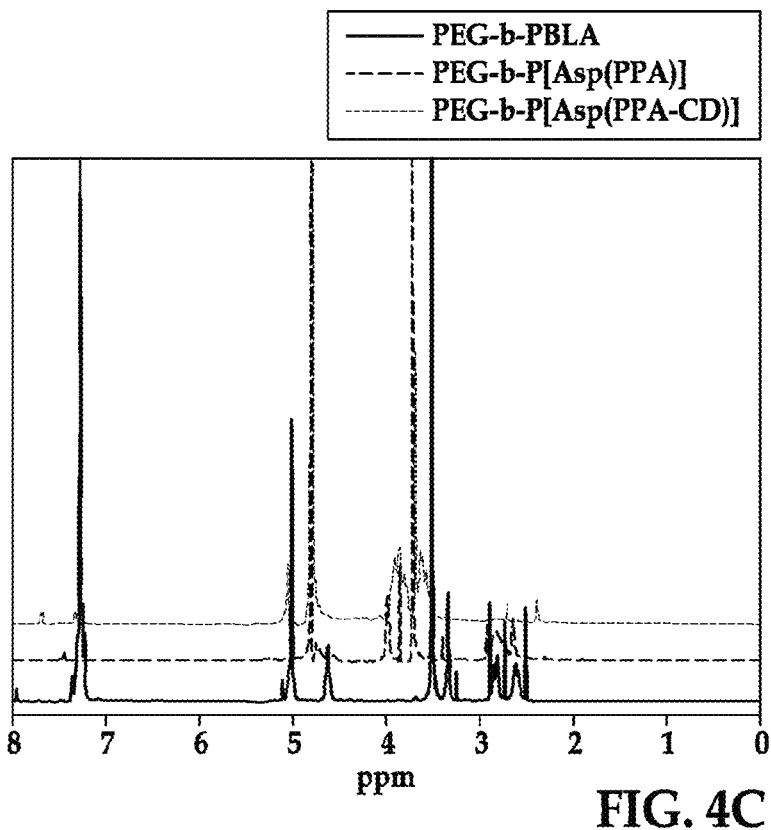

FIGS. 4B and 4C are FT-IR and $^1$H NMR spectra of PEG-b-P[Asp(PPA-CD)], which illustrate the successful introduction of β-cyclodextrin groups onto the side chain of PEG-b-P[Asp(PPA)].

As previously mentioned, any of the water soluble block or graft copolymers disclosed herein may be used to form assemblies with hydrophobic molecules or polymers. The assemblies are versatile carriers, at least in part because of the inclusion-capacity of cyclodextrin to many hydrophobic molecule(s) or polymer(s).

Such assemblies can be formed via a dialysis procedure. A mixture including a predetermined weight ratio of the copolymer and the hydrophobic molecule or polymer is dissolved in a common solvent. The solvent selected will depend, at least in part, on the copolymer and hydrophobic molecule or polymer selected. A non-limiting example of a suitable solvent is dimethyl sulfoxide (DMSO).

This solution is placed in dialysis tubing for dialysis against deionized water for a predetermined time at a predetermined temperature. The outer aqueous solution may be renewed as often as desired throughout the procedure. In a non-limiting example, the solution is renewed every 30 minutes for a portion of the predetermined time, and then every 120 minutes for the remainder of the predetermined time.

When using hydrophobic molecules as the guest, it is believed that the formation of the assemblies is mediated by host-guest interactions between the cyclodextrin units and the hydrophobic molecule. After the insertion of the hydrophobic molecule into the apolar cavity of the cyclodextrin units, the protruding portion provides the hydrophilic-hydrophilic block copolymer with localized hydrophobicity, which leads to the formation of a pseudo-amphiphilic block copolymer. As such, the hydrophobic molecules hydrophobilize the cyclodextrin unit containing block (i.e., the first hydrophilic block/graft chain) of the water soluble copolymer, thereby forming a hydrophobic core. The second hydrophilic block segment or graft chain forms a hydrophilic shell. Further assembly of this pseudo-amphiphilic copolymer in an aqueous solution forms the micelle-like assemblies. In some non-limiting examples, about one half of a pyrene molecule fills the apolar cavity of β-CD, while one or two coumarin 102 molecules fill the β-CD cavity. Furthermore, free hydrophobic molecules can be simultaneously encapsulated in the cores of assemblies due to the hydrophobic interaction.

When using polymers with hydrophobic groups as the guest, it is also believed that the host-guest interaction is responsible for the formation of the assemblies, considering the inclusion of hydrophobic groups by the cyclodextrin units. As the dialysis proceeds, the common solvent (e.g., DMSO) diffuses out and water diffuses into the polymer rich phase. The inclusion complexation of the cyclodextrin unit and the hydrophobic group decreases the surface tension between the guest polymer based particles and outer water phase, which prevents the otherwise large-scale aggregation of the hydrophobic polymers in the absence of the copolymer. As a result, free guest polymers and guest polymers associated with the first hydrophilic block/chain block form the cores of resultant particles, while the second hydrophilic block/chain acts as a hydrophilic shell to stabilize the assemblies.

Non-limiting examples of the guest molecule include pyrene, coumarin, adamantine-carboxylic acid (ADCA), rapamycin (RAP), dexamethasone (DMS), ibuprofen (IBU), or indomethacin (IND), and non-limiting examples of the guest polymer include poly(β-benzyl L-aspartate), polystyrene, or poly(D,L-lactide). While these specific examples are listed herein, it is to be understood that other hydrophobic small molecule, polymers, or charge-containing species such as proteins, peptides, hormones, DNAs, RNAs, siRNAs, therapeutic drugs, nutrients, pigments, fertilizers, fragrances, food additives, or the like may be utilized as or be associated with the guest molecule/polymer.

It is to be understood that hydrophobic or charged molecule or polymer loading capabilities and release profiles of the assemblies may be manipulated by changing the type of hydrophobic or charged molecule/polymer, the biodegradability of the hydrophobic or charged molecule/polymer, the pH of the hydrophobic or charged molecule/polymer, the temperature sensitivity of the hydrophobic or charged molecule/polymer, or other characteristics of the hydrophobic or charged molecule/polymer, or combinations thereof. Furthermore, it is to be understood the size of the assembly may be partially controlled by the weight content of the guest hydrophobic or charged molecule/polymer.

To further illustrate embodiments of the present disclosure, the following examples are given herein. It is to be understood that these examples are provided for illustrative purposes and are not to be construed as limiting the scope of the disclosed embodiments.

EXAMPLES

Example 1

PEG-b-PCD Assemblies with Hydrophobic Molecules

A diblock hydrophilic copolymer was characterized by tandem alignment of a polyethylene glycol block and a polyaspartamide block carrying β-cyclodextrin units on the side chain. This copolymer was used to form assemblies with pyrene, coumarin 102, or rapamycin.

Synthesis of PEG-b-Polyaspartamide Containing EDA Unit (PEG-PEDA)

The formation of the diblock hydrophilic copolymer of this example began with the synthesis of PEG-b-polyaspartamide containing an EDA unit (PEG-PEDA). BLA-NCA was polymerized in DMF at 40° C. by the initiation from the terminal primary amino group of MPEG-$NH_2$ to obtain PEG-b-PBLA. The degree of polymerization (DP) of PBLA was calculated to be 15 based on $^1$H NMR spectroscopy. PEG-b-PEDA was prepared through the quantitative aminolysis reaction of PEG-b-PBLA in dry DMF at 40° C. in the presence of 50-fold the molar concentration of EDA. After 48 hours, the reaction mixture was dialyzed against deionized water (MWCO: 3500), and the final aqueous solution was lyophilized to obtain white powder.

Synthesis of PEG-b-PCD

Lyophilized PEG-b-PEDA (600 mg) and 5 fold excess amount of 6-monotosyl β-cyclodextrin were reacted in 30 ml anhydrous DMSO. After 5 days, the reaction mixture was dialyzed against 0.1 N NaOH for 2 days to remove unreacted 6-monotosyl β-cyclodextrin, and then dialyzed against distilled water for 2 days. The reaction product was filtered through a 0.22 μm syringe filter, and the resultant aqueous solution was lyophilized to obtained brown powder.

Figure 5:
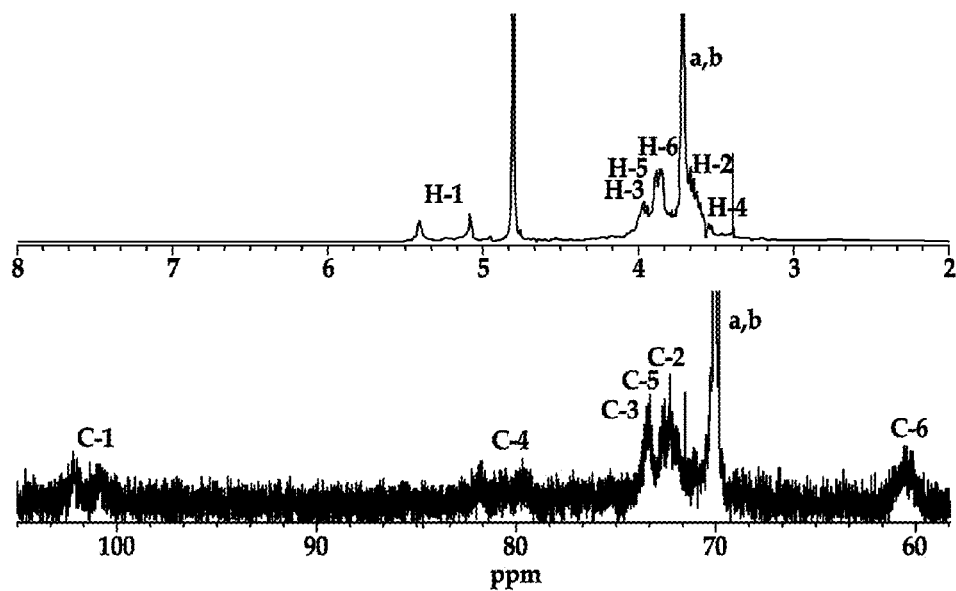
FIG. 5 illustrates the $^1$H NMR spectrum in $D_2O$ (top) and the $^{13}$C NMR spectrum in DMSO-$d_6$ (bottom) of PEG-b-PCD.
Figure 6:
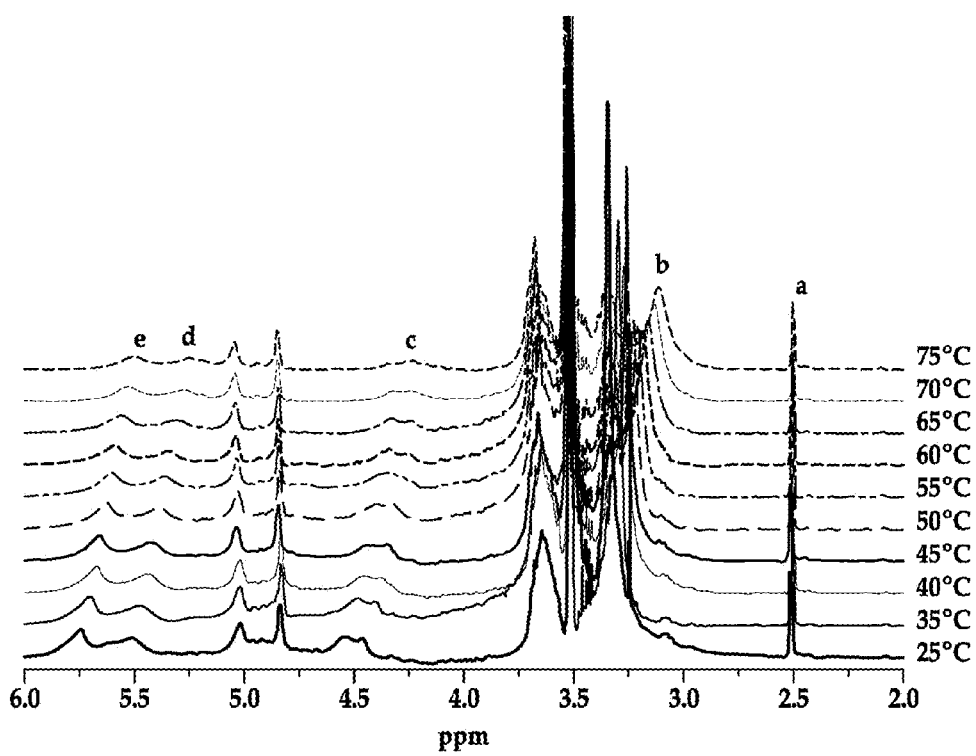
FIG. 6 illustrates the $^1$H NMR spectra of PEG-b-PCD in DMSO-$d_6$ measured at various temperatures, where the following peaks are labeled: a, residual solvent (DMSO) peak; b, trace of $H_2O$ in DMSO-$d_6$; c, proton signal from OH group connected with C-6 of cyclodextrin as shown in FIG. 5; d, proton signal from OH group connected with C-3 of cyclodextrin as shown in FIG. 5; e, proton signal from OH group connected with C-2 of cyclodextrin as shown in FIG. 5.

$^1$H and $^{13}$C NMR spectra of PEG-b-PCD are shown in FIG. 5. Calculation based on $^1$H NMR spectrum suggests that about 10 β-cyclodextrin molecules were introduced into the side chains of PEDA segment. The resultant polymer can be easily dissolved in water at room temperature. It can also be well dissolved in DMSO when heated to about 50° C. as evidenced by temperature dependent $^1$H NMR spectra in DMSO-$d_6$ (FIG. 6). In FIG. 6, the temperature dependent chemical shift of peaks corresponds to $H_2O$ and hydroxyl groups in β-CD. Chemical shift was referenced according to DMSO peak at 2.5 ppm. For sample preparation, PEG-b-PCD was first dissolved in DMSO-$d_6$ by heating to 60° C. After being cooled to room temperature (about 23° C.), spectra at various temperatures were acquired.

Preparation of Host-Guest Assemblies

PEG-b-PCD based polymeric assemblies containing small molecules including, respectively, pyrene, coumarin 102, and rapamycin were prepared via a dialysis method. Mixtures of each small molecule substance and the copolymer with a certain weight ratio were co-dissolved in dimethylsulfoxide (DMSO) at 50° C. with a final polymer concentration of 10 mg/ml. In particular, for the PEG-b-PCD based polymeric assemblies containing rapamycin, 5 mg of rapamycin and 15 mg of PEG-b-PCD were co-dissolved in 1.5 ml DMSO at 50° C. Similarly, for the PEG-b-PCD based polymeric assemblies containing pyrene or coumarin 102, 5 mg of pyrene or coumarin 102 and 15 mg of PEG-b-PCD were co-dissolved in 1.5 ml DMSO at 50° C. Each solution was placed into a dialysis tubing (MWCO 6-8 kDa) for dialysis against deionized water for 24 hours at 25° C. The outer aqueous solutions were renewed every 30 min for the first 2 hours, and then every 2 hours for the remaining period of time. The dialysis solutions were filtered through a 0.45 μm syringe filter. The weight content of pyrene, coumarin 102, or rapamycin was quantified by UV-Vis measurement.

PEG-b-PCD/Pyrene Host/Guest Assemblies

Figure 7A:
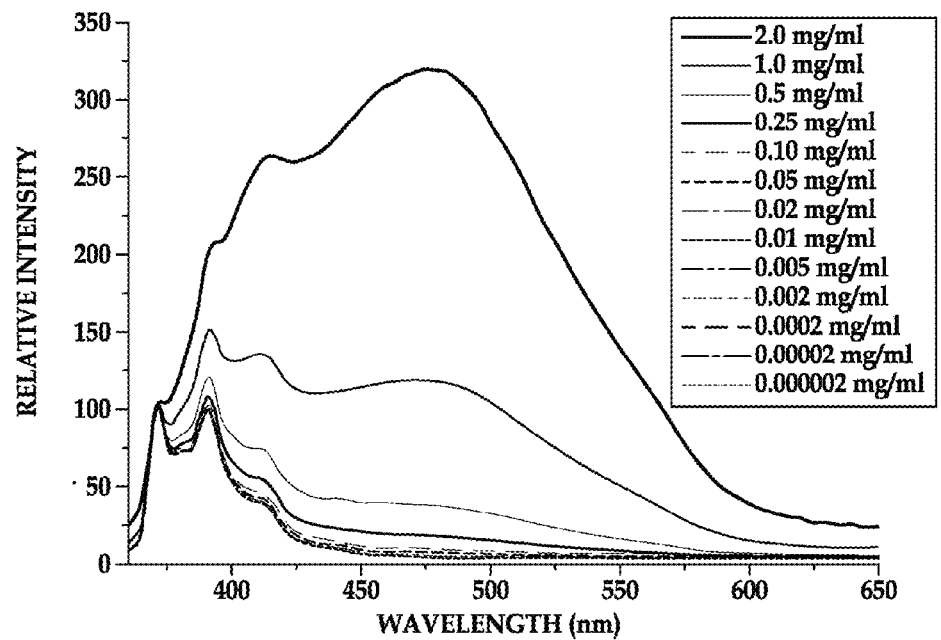
FIGS. 7A-7D illustrate the normalized emission spectra of pyrene in aqueous solutions containing various concentrations of PEG-b-PCD (6A and 6B) and β-CD (7C and 7D), where
Figure 7B:
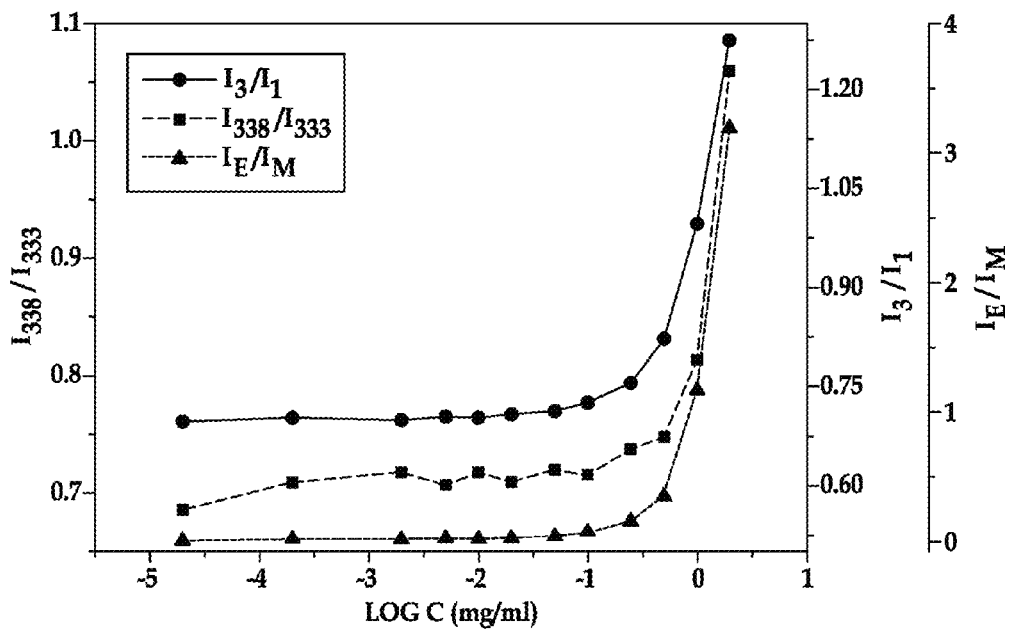
Figure 7C:
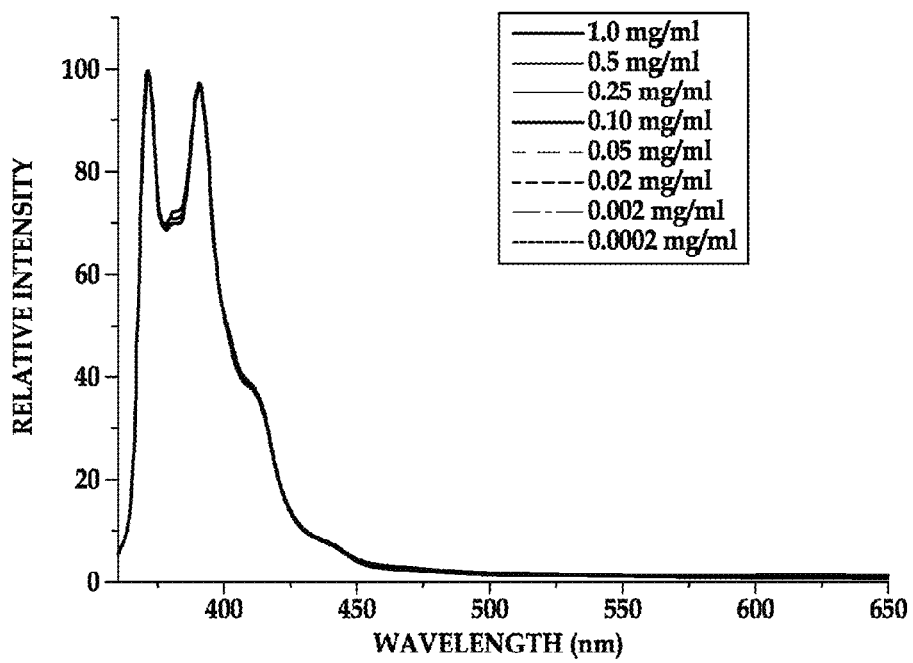

The intrinsic photophysical characteristics of pyrene make it possible to directly characterize the polymeric assemblies through fluorescence technique. The normalized emission spectra of pyrene in aqueous solutions in the presence of various concentrations of PEG-b-PCD or β-CD are shown in FIGS. 7A through 7D. The fluorescence band from 370 nm to 420 nm is the characteristic emission of excited pyrene monomer, while the broad band extending from 420 nm to 600 nm is ascribed to the pyrene excimer. With the increase in PEG-b-PCD concentration, a significant enhancement in excimer intensity is observed. In the case of β-CD, however, no excimer formation is observed (FIG. 7C). Excimer formation is a short range phenomenon (3-5 Å). Pyrene excimers are formed either by the collision between excited and ground-state monomers, or by the excitation of pre-associated pyrene pairs in the ground-state. If it were the former process, excimer formation should have also been observed for the β-CD solution considering the equal pyrene concentration in these systems. However, no excimer was observed from pyrene in the presence of various concentrations of β-CD. The broadening of the excitation band of pyrene in the presence of PEG-b-PCD supports the ground-state dimer formation (see FIG. 8).

Figure 8:
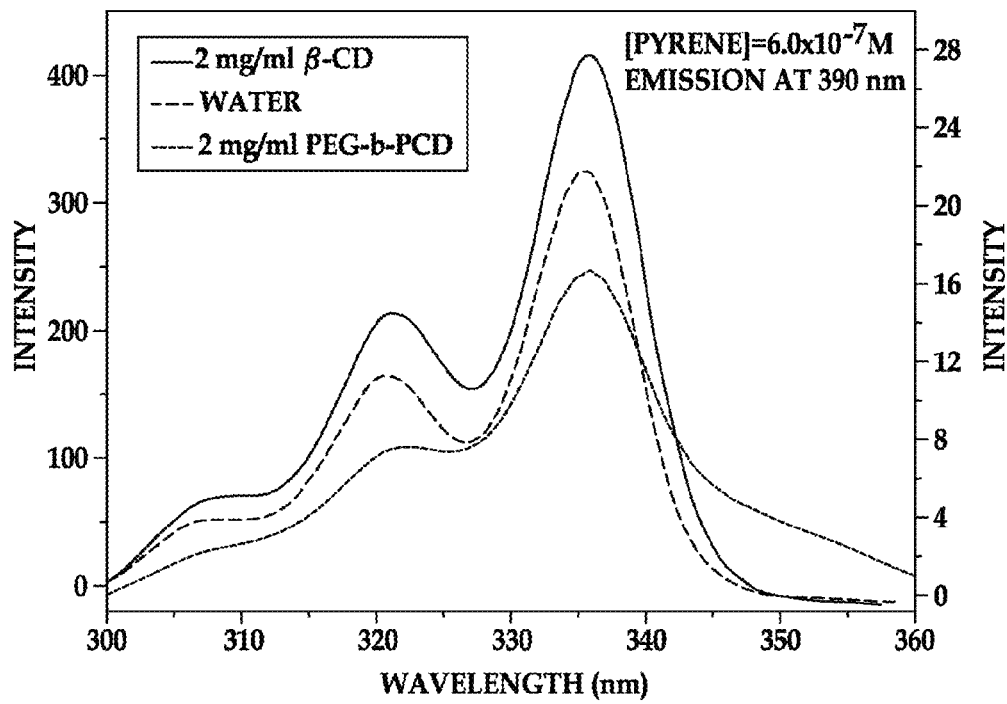
FIG. 8 illustrates the excitation spectra of pyrene in aqueous solutions containing various substances.

As shown in FIG. 8, the introduction of β-CD leads to an enhancement of fluorescence intensity of pyrene in aqueous solution, while the shape of excitation spectrum is scarcely altered by the β-CD. The addition of PEG-b-CD substantially alters the shape of the excitation spectrum (the spectrum becomes broad and the excitation edge shifts towards long wavelength). The increase in excitation intensity when CD is added is believed to be due to the dissolution of pyrene adsorbed to the walls of the container, taking into consideration the inclusion effect of CD to pyrene.

Figure 7D:
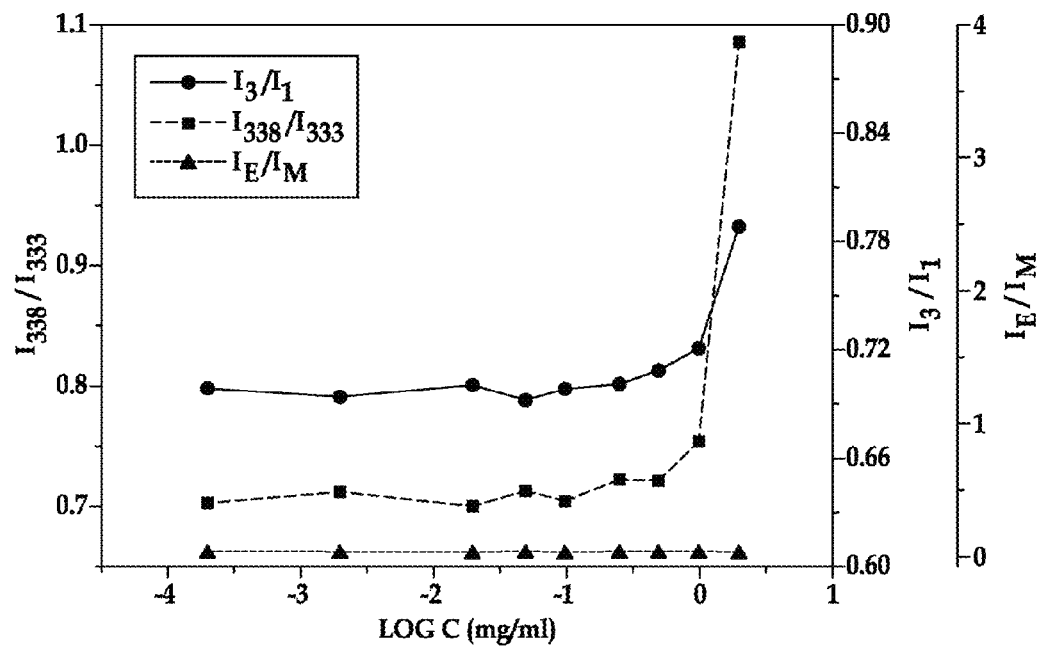
Figure 9:
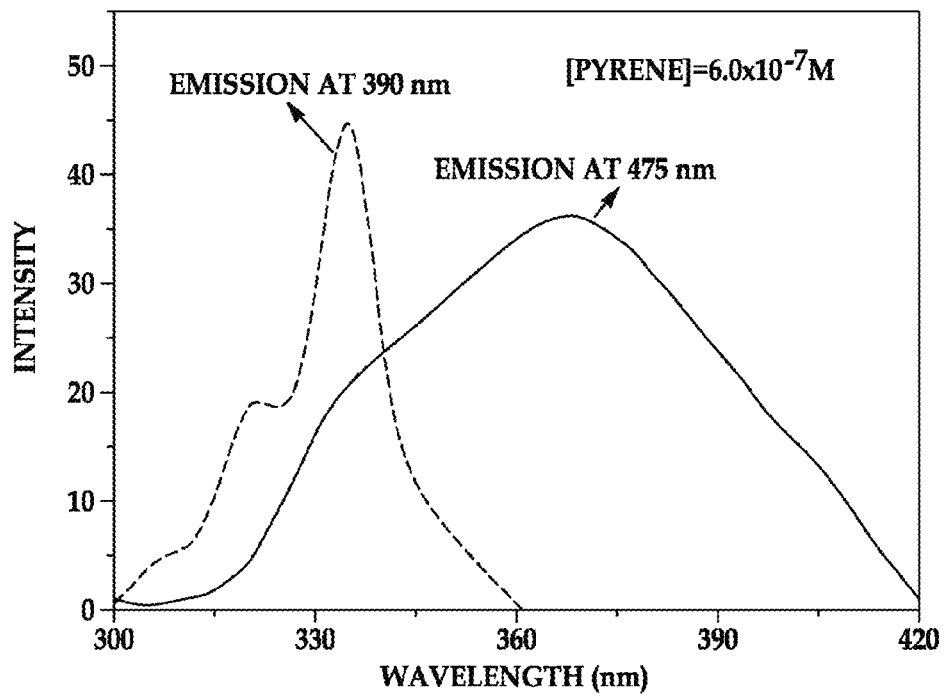
FIG. 9 illustrates the fluorescence excitation spectra of pyrene in aqueous solution in the presence of PEG-b-PCD (1.0 mg/ml), which were monitored at 390 and 475 nm separately.

Additionally, the significant decrease in excitation fluorescence in PEG-b-PCD solution likely results from the quenching phenomenon, suggesting the existence of a local high concentration of pyrene. As shown in FIG. 9, the excitation spectrum of pyrene in the presence of PEG-b-PCD monitored at excimer fluorescence band (475 nm) is significantly different from that monitored at the monomer wavelength (390 nm). The former spectrum shows a significant bathochromic shift with the broadening in vibrational structure. This result also supports the ground-state dimer formation of pyrene. Plots of concentration dependent changes in intensity ratios of I338/I333, I3/I1 and IE/IM are shown in FIGS. 7B and 7D because these values are indicative of the local environment of pyrene. Significant increase in the values of I338/I333, I3/I1 and IE/IM can be observed for pyrene as the concentration of PEG-b-PCD increased to a certain point (FIG. 7B). No significant changes in IE/IM, however, were found in the case of β-CD (FIG. 7D). Furthermore, the values of I3/I1 for PEG-b-PCD are significantly larger than those for β-CD. These observations indicate that pyrene molecules locate themselves in a more hydrophobic microenvironment in the existence of PEG-b-PCD.

Pyrene (width=8.2 Å; length=10.4 Å) is able to form either 1:1 or 1:2 complex with β-CD (internal diameter=7.8 Å) depending, at least in part, on the β-CD concentration. The apolar cavity of β-CD is believed to be responsible for the changes in fluorescence spectra of pyrene molecules in aqueous solutions containing β-CD. For pyrene molecules in an aqueous solution of PEG-b-PCD, in addition to the apolar cavity of β-CD, association of pyrene molecules should also contribute to the enhanced local hydrophobicity as evidenced by excimer formation. These results suggest that PEG-b-PCD forms micelle-like assemblies in the presence of hydrophobic pyrene. The cyclodextrin-containing block, which forms an inclusion complex with pyrene, is believed to construct the cores of the assemblies, while the extended PEG chains is believed to serve as a hydrophilic shell.

Figure 10A:
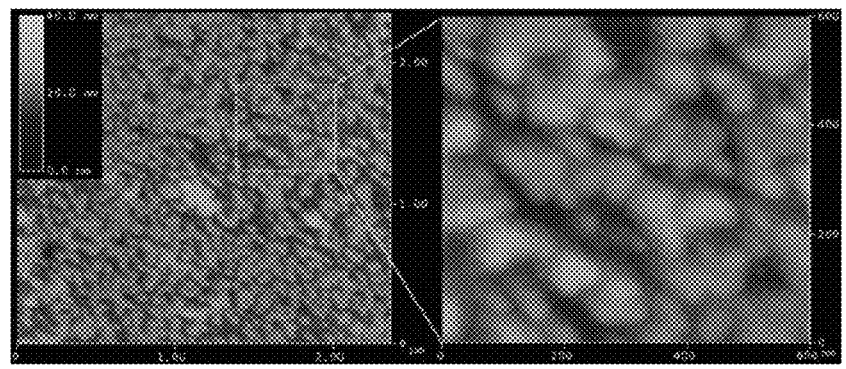
FIG. 10A illustrates height tapping-mode AFM (atomic force microscopy) images of PEG-b-PCD assemblies containing pyrene.
Figure 10B:
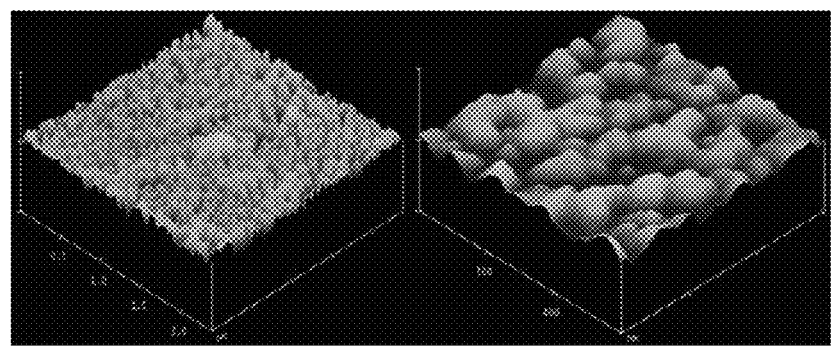
FIG. 10B illustrates 3D tapping-mode AFM images of PEG-b-PCD assemblies containing pyrene.
Figure 10C:
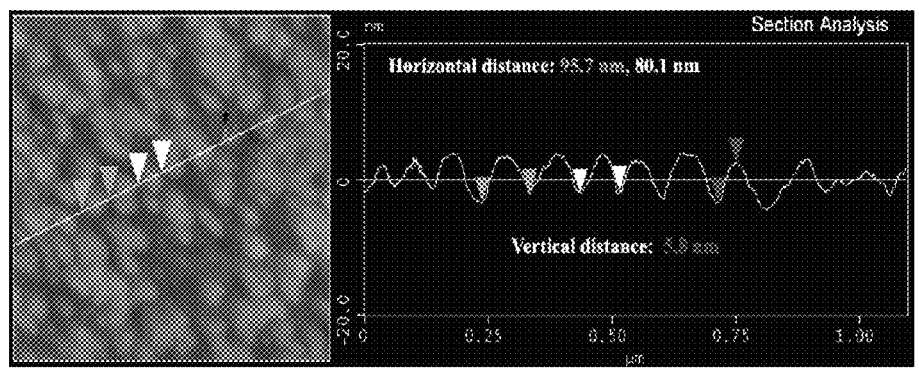
FIG. 10C is the cross-sectional analysis of PEG-b-PCD assemblies containing pyrene.
Figure 11:
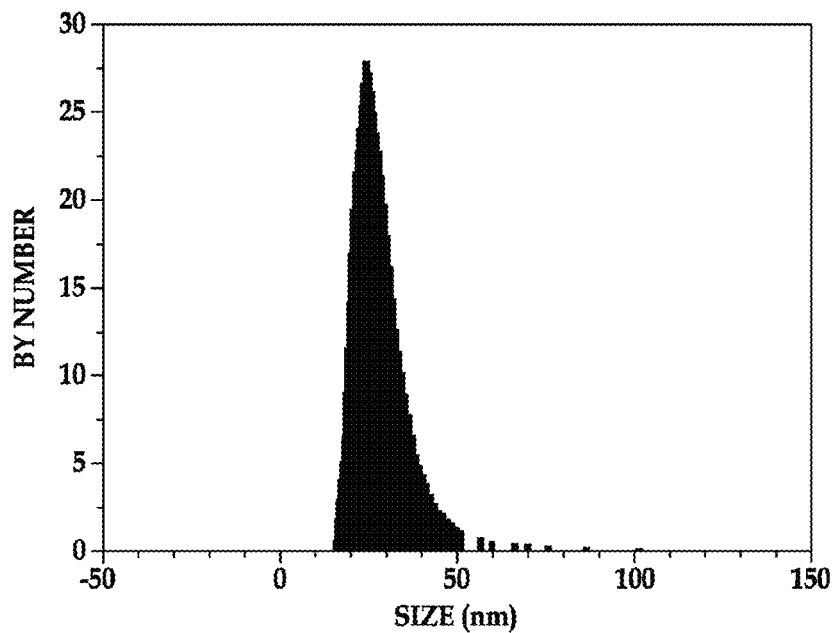
FIG. 11 is a particle size distribution graph of PEG-b-PCD assemblies containing pyrene.
Figure 12:
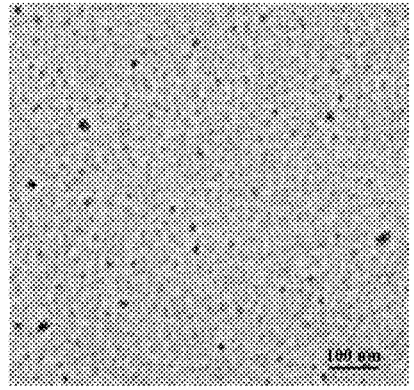
FIG. 12 is a TEM (transmission electron microscopy) image of PEG-b-PCD assemblies containing pyrene.

The weight content of pyrene in the assembly was about 0.6%, as determined by UV measurement. The morphological properties of these assemblies were initially examined by atomic force microscopy (AFM). Height and 3D AFM images of the PEG-b-PCD assemblies containing pyrene obtained from the aqueous solution (total concentration: 2 mg/ml) are shown in FIGS. 10A and 10B. These AFM images show assemblies of a round shape with diameters ranging from 20 nm to 120 nm. AFM sectional analysis (FIG. 10C, for example) of a typical structure shows that the diameters of the assemblies are generally ten-to seventeen-times larger than the heights of the aggregates. It is believed that this is attributable to the flattening of spherical particles following adsorption onto the mica surface and indicates that these assemblies are soft enough to deform upon drying, which is further confirmed by dynamic light scattering (DLS) and transmission electron microscopy (TEM) measurements. Calculation based on several AFM images gives a mean size of 63.5 nm, while DLS measurement shows a mean number-average diameter of 27.3 nm (FIG. 11). In addition, TEM images reveal the mean diameter of pyrene-containing assemblies to be about 20.0 nm (FIG. 12), which is well consistent with the DLS result.

PEG-b-PCD/Coumarin 102 Host/Guest Assemblies

Figure 14:
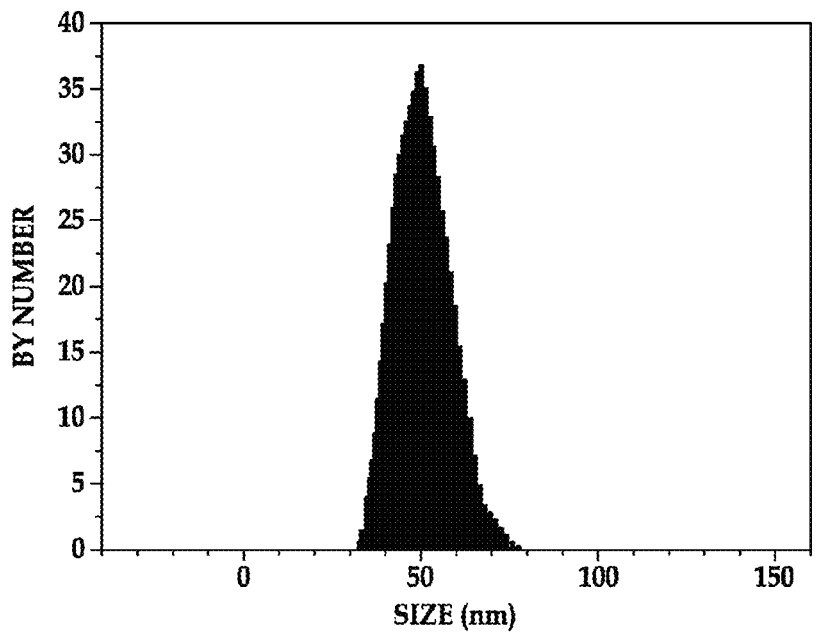
FIG. 14 is a particle size distribution graph of PEG-b-PCD assemblies containing coumarin 102.
Figure 15:
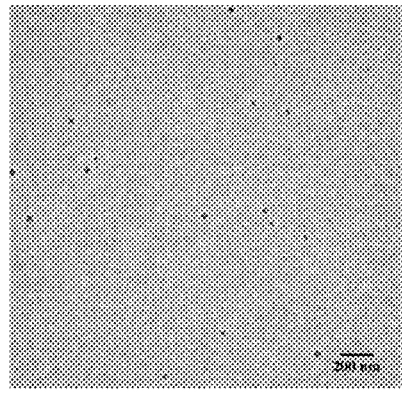
FIG. 15 is a TEM image of PEG-b-PCD assemblies containing coumarin 102.
Figure 13A:
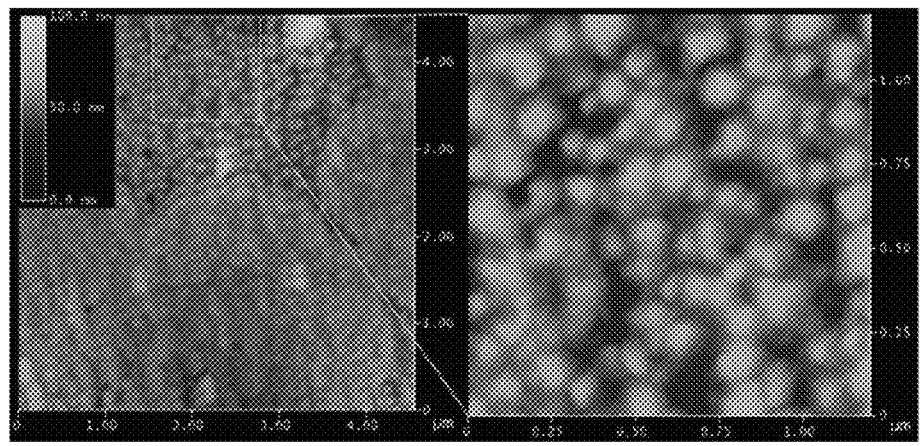
FIG. 13A illustrates height tapping-mode AMF images of PEG-b-PCD assemblies containing coumarin 102.
Figure 13B:
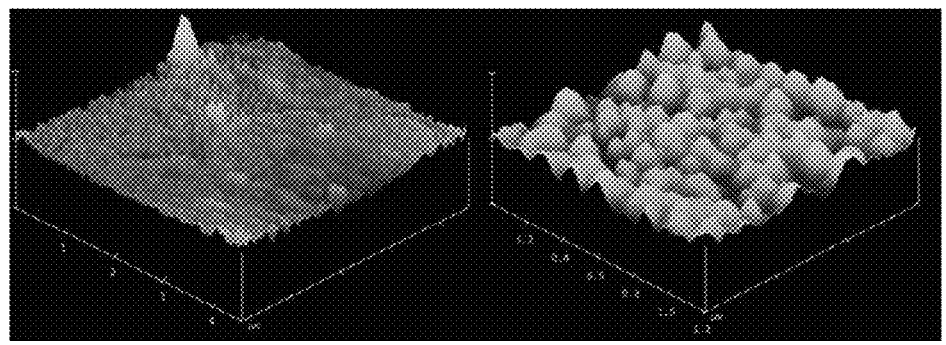
FIG. 13B illustrates 3D tapping-mode AMF images of PEG-b-PCD assemblies containing coumarin 102.
Figure 13C:
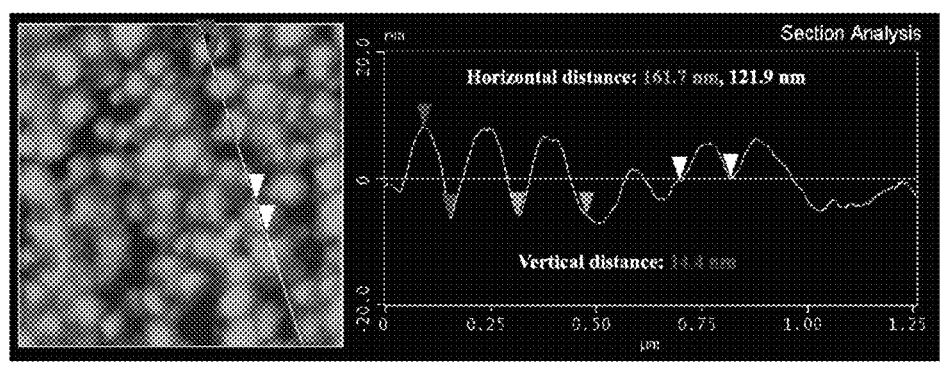
FIG. 13C is the cross-sectional analysis of PEG-b-PCD assemblies containing coumarin 102.

The content of coumarin 102 in the assembly quantified by UV-Vis measurement was about 1.2 wt %. The morphology and particle size were also characterized by AFM, TEM and DLS. Height and 3D AFM images of the PEG-b-PCD assemblies containing coumarin 102 obtained from the aqueous solution (total concentration: 2 mg/ml) are shown in FIGS. 13A and 13B. AFM images show assemblies of a round shape with a mean number-average diameter of 108.4 nm. Sectional analysis (FIG. 13C) shows the relatively larger ratio of diameter to height (7~15), which is similar to that observed for pyrene-containing assemblies, and the flattening effect is believed to contribute to this morphological deformation. This result suggests that this type of assembly exhibited loose inner cores. DLS determination shows the mean number-average diameter to be 49.9 nm (FIG. 14). Such results are consistent with the TEM result (~38 nm) as shown in FIG. 15.

PEG-b-PCD/Rapamycin Host/Guest Assemblies

The content of rapamycin in the assembly quantified by UV-Vis measurement was about 9.3 wt %. It is to be understood that this may be different for different experimental conditions and compositions.

Figure 16:
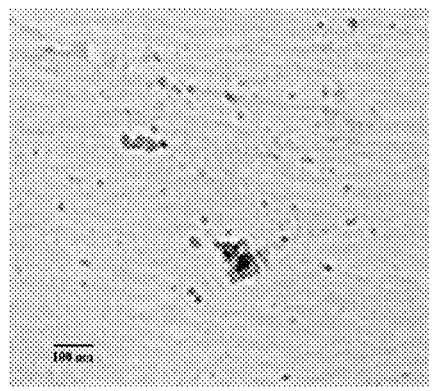
FIG. 16 is a TEM image of PEG-b-PCD assemblies containing rapamycin.

Transmission electron microscopy (TEM) observation was carried out on a JEOL-3011 high resolution electron microscope operating at an acceleration voltage of 300 kV. Formvar coated copper grids, stabilized with evaporated carbon film, were used. Samples for TEM preparation were prepared at 25° C. by dipping the grid into the aqueous solution of PEG-b-PCD/rapamycin host/guest assemblies. Extra solution was blotted from the grid with filter paper. After the water was evaporated at room temperature for several days, the samples were observed directly without any staining. The rapamycin-containing nanospheres have a size scale of about 10 nm (see FIG. 16)

Figure 17:
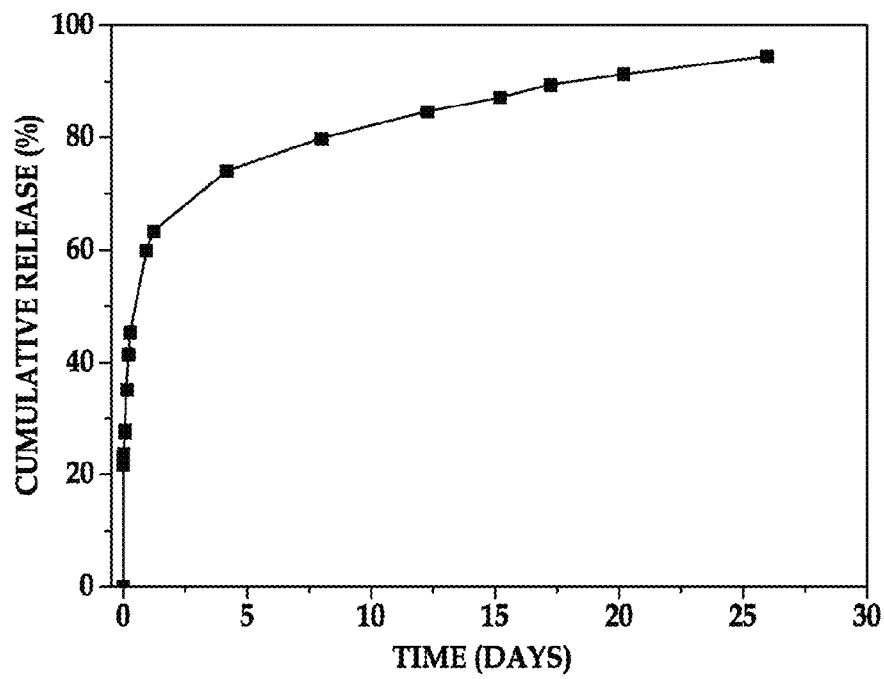
FIG. 17 is a graph depicting the in vitro release of rapamycin from assemblies based upon PEG-b-PCD.

10 mg of lyophilized rapamycin-containing assemblies was dissolved into deionized water, and placed into dialysis tubing. The amount of assemblies may also be varied, for example, from a few mg to hundreds of mg). The loaded dialysis tubing was immerged into 30 ml phosphate buffered saline (PBS, 0.1M, pH 7.4). At predetermined time intervals (ranging from minutes to hours to days to weeks to months), 4.0 ml of the release medium was withdrawn, and fresh PBS was added. The rapamycin concentration in the release buffer was determined using UV at 278 nm. The release profile indicates a fast release in the first week followed by a slower sustained release for about 3 additional weeks (see FIG. 17).

PEG-b-PCD/Model drug Host/Guest Assemblies

Figure 18:
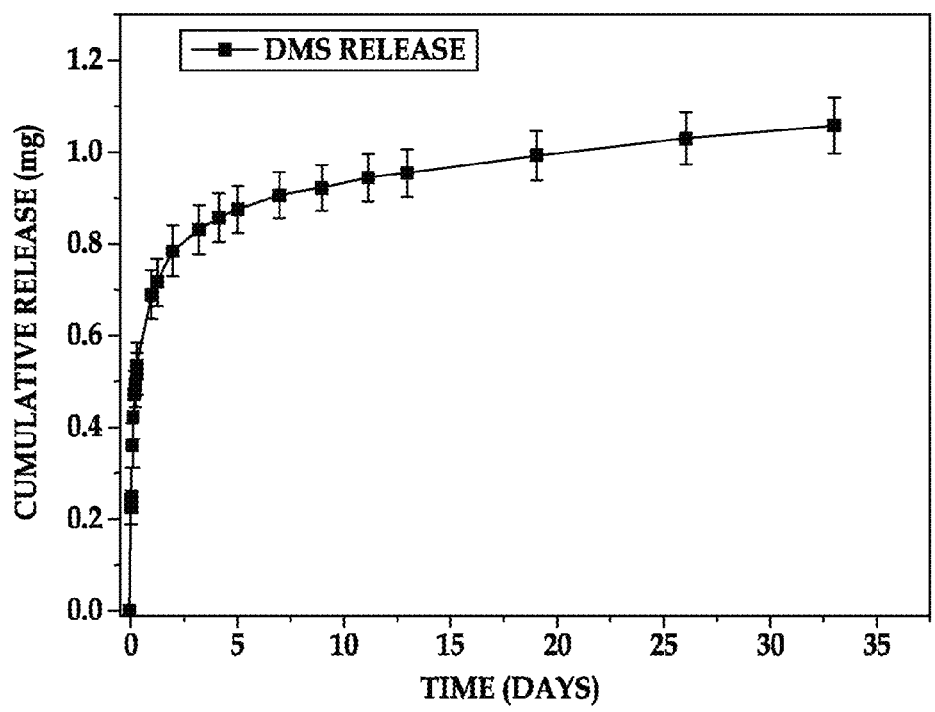
FIGS. 18-20 are in vitro release profiles of various drugs from PEG-b-PCD assemblies.
Figure 19:
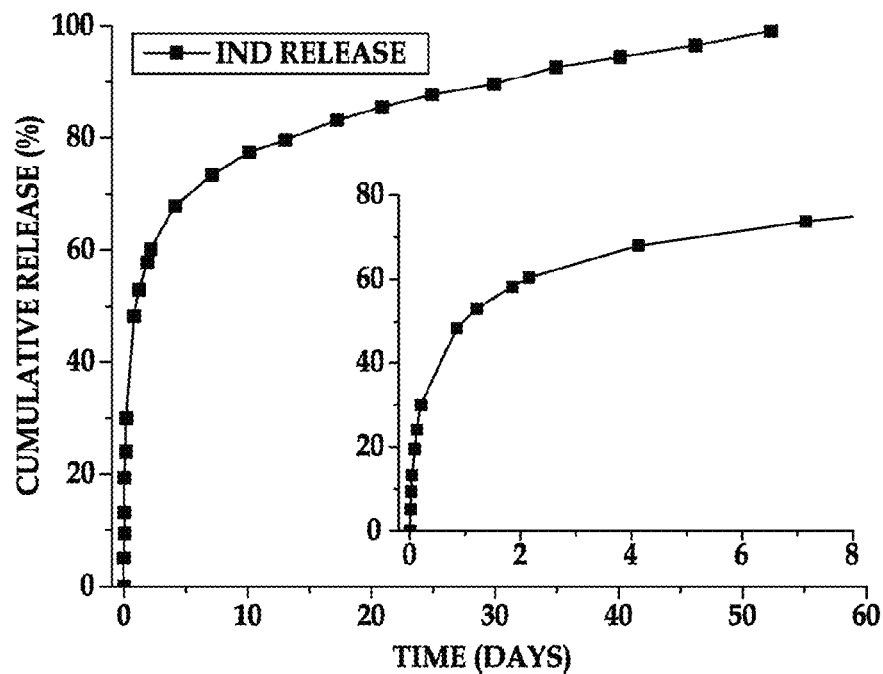
Figure 20:
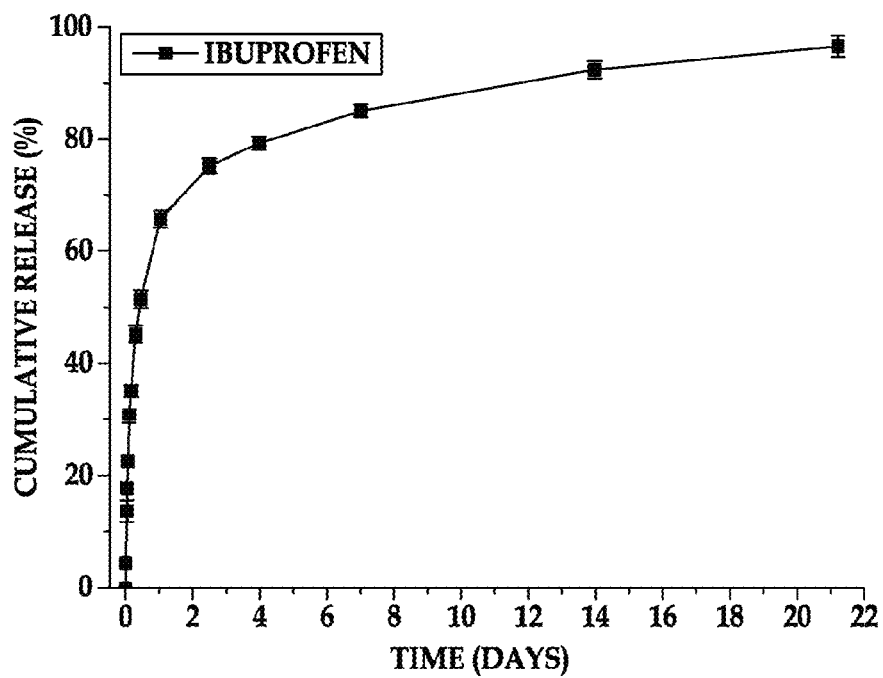

PEG-b-PCD based polymeric assemblies containing small molecules including model drugs (dexamethasone (DMS), indomethacin (IND), and ibuprofen (IBU)) were prepared similarly to the formation of the PEG-b-PCD/rapamycin host/guest assemblies as described in this Example. Each of these assemblies was subjected to an in vitro release study. 10 mg of lyophilized dexamethasone-containing assemblies, indomethacin-containing assemblies, and ibuprofen containing assemblies was dissolved into respective deionized water samples, and placed into respective dialysis tubings. The amount of assemblies may also be varied, for example, from a few mg to hundreds of mg). The loaded dialysis tubings were immerged into 30 ml phosphate buffered saline (PBS, 0.1M, pH 7.4). At predetermined time intervals (ranging from minutes to hours to days to weeks to months), 4.0 ml of the respective release media was withdrawn, and fresh PBS was added. The dexamethasone, indomethacin, or ibuprofen concentration in the release buffer was determined using UV at 278 nm. The release profile for dexamethasone indicates a fast release in the first two weeks followed by a slower sustained release for about 2 additional weeks (see FIG. 18). The release profile for indomethacin indicates a fast release in the first week followed by a slower sustained release for about 3 additional weeks (see FIG. 19). The release profile for ibuprofen indicates a fast release in the first week followed by a slower sustained release for about 2 additional weeks (see FIG. 20).

Example 2

PEG-b-PCD Assemblies with Hydrophobic Polymers

PEG-b-PCD was synthesized using the procedure outline above in Example 1.

The hydrophobic polymers used were poly(β-benzyl L-aspartate) (PBLA) with a number-average molecular weight of 2000 (the degree of polymerization is about 10), synthesized by ring-opening polymerization, and poly(D,L-lactide) (PDLLA).

Figure 21A:
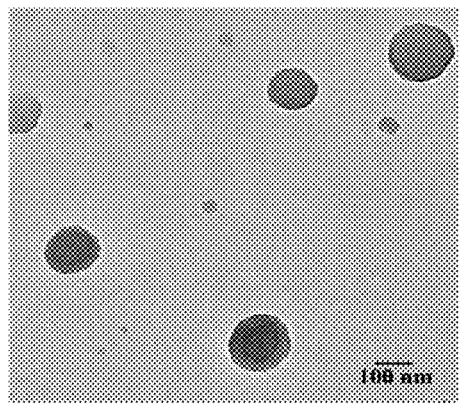
FIGS. 21A-21C are images (21A and 21C are TEM images and 21B is an FE-SEM image) of PEG-b-PCD assemblies containing PBLA, where
Figure 21B:
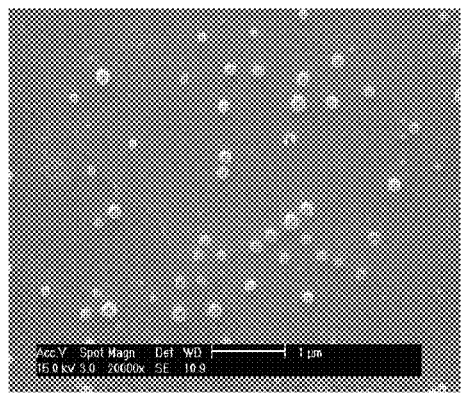
Figure 21C:
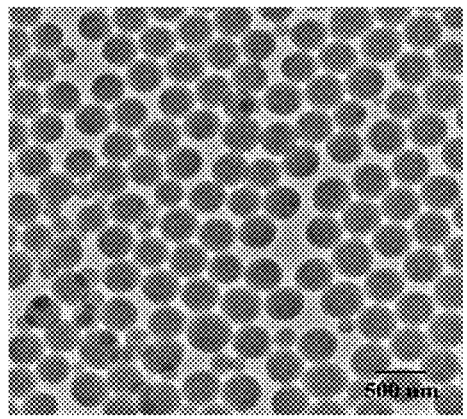
Figure 22A:
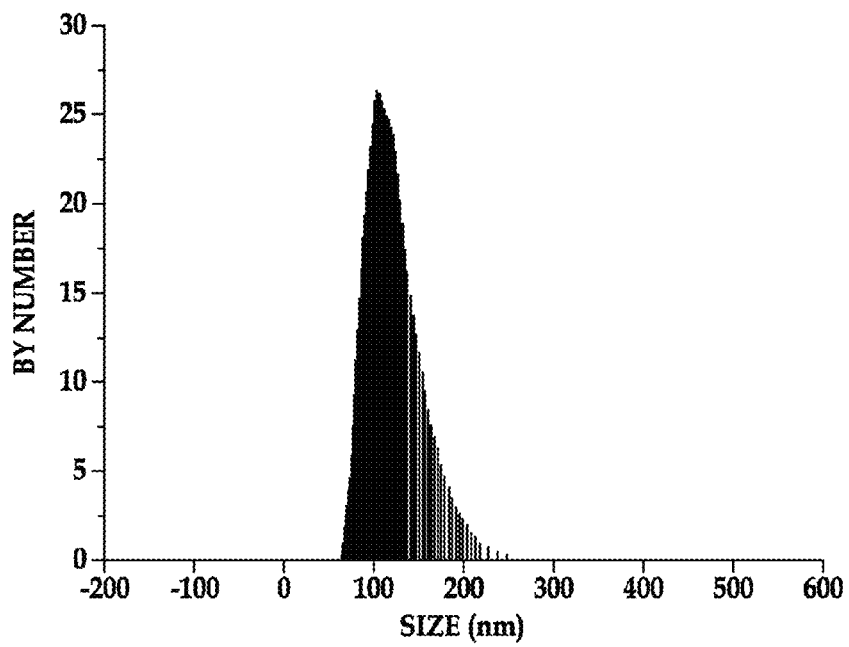
FIGS. 22A and 22B are particle size distribution graphs of PEG-b-PCD assemblies containing PBLA, where PBLA: PEG-b-PCD ratio is 1:20 in FIG. 22A and PBLA:PEG-b-PCD ratio is 8:20 in FIG. 22B.

For the assemblies based on PEG-b-PCD and the hydrophobic polymers, the same procedure was employed as described in Example 1, with the following variations: PEG-b-PCD, PBLA, or PDLLA was separately dissolved in DMSO at 50° C.; the mixture solution with an appropriate weight ratio of PEG-b-PCD/PBLA or PEG-b-PCD/PDLLA was dialyzed against deionized water for one day; and the dialysis solution was filtered through a 0.45 μm syringe filter.
PEG-b-PCD/PBLA Host/Guest Assemblies The physicochemical characteristics of the assemblies were investigated by TEM, DLS, and field-emission scanning electron microscopy (FE-SEM). As shown in FIG. 21A, spherical assemblies with mean diameters ranging from 50 nm to 200 nm were obtained with a theoretical feed ratio of 1:20 (weight ratio of PBLA to PEG-b-PCD), and particle size analysis based on TEM images indicates the mean size to be about 96.4 nm. This value corresponds with that determined by DLS (118.7 nm) as shown in FIG. 22A. FIG. 21B illustrates the FE-SEM image, which suggests the mean size is about 256.7 nm. It is believed that these differing results are due to the flattening of the assemblies when they were dried on the mica surface, similar to PEG-b-PCD based assemblies containing pyrene or coumarin 102. FIG. 21C illustrates a TEM image for assemblies prepared with a feed ratio of 8:20, and it is noted that the particle size increased significantly.

Figure 22B:
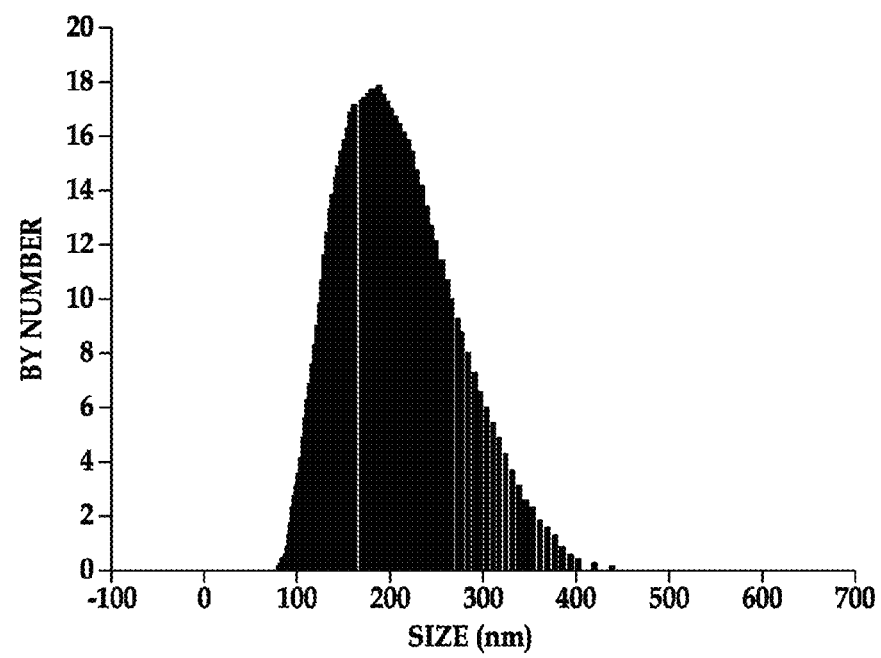

The mean size for the assemblies shown in FIG. 22B was determined by DLS to be 209.2 nm.

Figure 23:
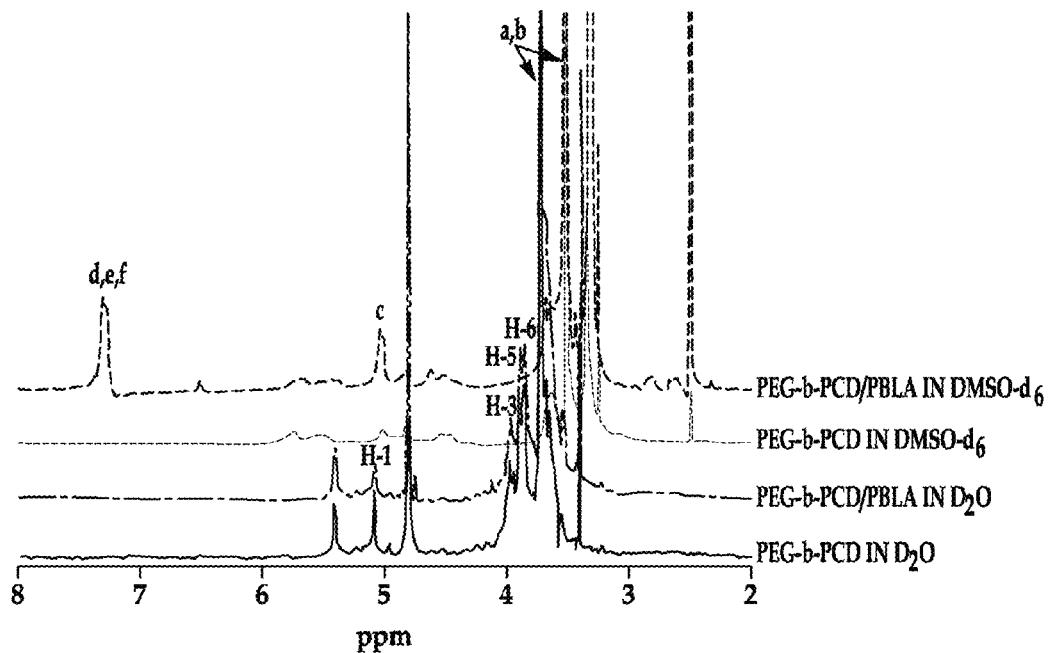
FIG. 23 illustrates the $^1$H NMR spectra of PEG-b-PCD and PEG-b-PCD based assemblies containing PBLA in $D_2O$ or DMSO-$d_6$.

The cores of the PEG-b-PCD/PBLA assemblies were investigated by $^1$H NMR and fluorescence anisotropy. For the NMR characterization, PEG-b-PCD assemblies with PBLA were prepared by dialysis (as described above) and the resultant aqueous solution was lyophilized. The dried sample was dissolved into $D_2O$, and $^1$H NMR spectrum was acquired. The same sample was subjected to NMR measurement after it was lyophilized and dissolved in DMSO-$d_6$. As shown in FIG. 23, no signals corresponding to PBLA were observed for assemblies based on PEG-b-PCD and PBLA in $D_2O$. However, signals at 7.3 and 5.0 ppm that are characteristic peaks of protons corresponding to benzyl group, are evident in DMSO. This indicates that the cores of these assemblies are mainly comprised of PBLA.

Figure 25:
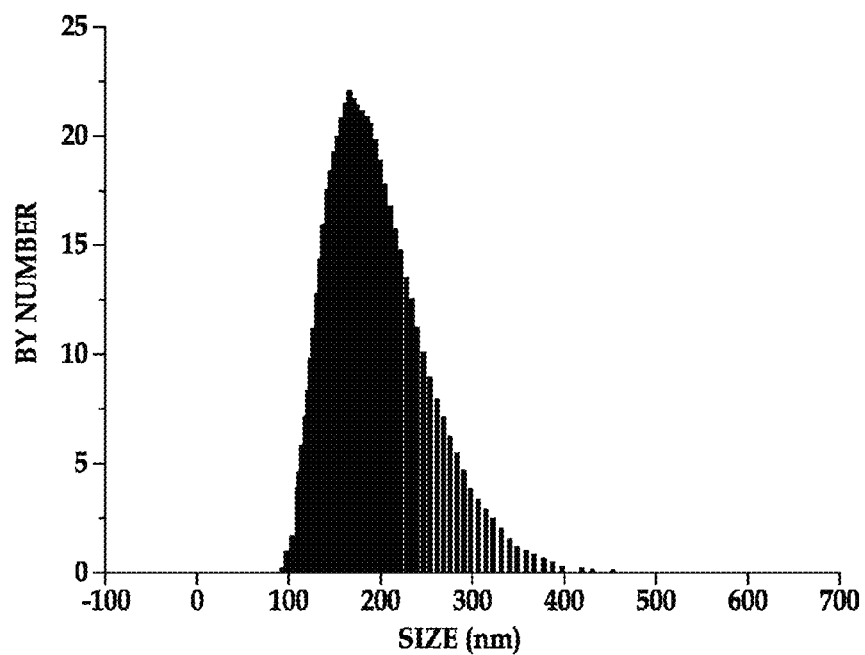
FIG. 25 is a particle size distribution graph of PEG-b-PCD assemblies containing PDLLA.
Figure 24:
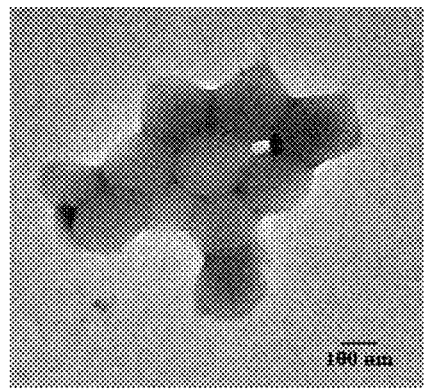
FIG. 24 is a TEM image of PEG-b-PCD assemblies containing PDLLA.

Further information on the microviscosity of the inner core was provided by the depolarization of fluorescence using 1,6-diphenyl-1,3,5-hexatriene (DPH) as the fluorophore. Anisotropy value (r) of a fluorescent probe is correlated with the viscosity of microenvironment where the probe molecules locate in, and a higher value of r indicates that the microdomains are more viscous. The value of r measured for DPH in an aqueous solution of PEG-b-PCD based assemblies containing PBLA is 0.2, while r is 0.25 for aqueous solution of micelles based on poly(ethylene glycol)-b-poly(β-benzyl L-aspartate). As such, the former exhibits almost the same microviscosity as that of the latter. These results demonstrate that the cores of assemblies based on PEG-b-PCD and PBLA are essentially rigid. The rigid cores provide these assemblies with dynamic stability against dilution, which may be desirable for drug delivery systems based on polymeric assemblies to be administered by systemic injection. Furthermore, lyophilized samples of assemblies based on PEG-b-PCD and PBLA can be re-dispersed in water without significant increase in mean particle size.
PEG-b-PCD/PDLLA Host/Guest Assemblies FIG. 24 illustrates a TEM image of assemblies based on PEG-b-PCD and PDLLA. The mean size calculated according to the TEM images is 153.6 nm, which well agrees with the magnitude determined by DLS (184.3 nm, FIG. 25).

Example 3

PEG-b-PCD Polyion Complex Assemblies

PEG-b-PCD was synthesized using the procedure outline above in Example 1.

Polyion complex (PIC) micelles may be used as delivery systems for metal complexes, water soluble peptides and proteins, and genes. As such, adamantane-carboxylic acid (ADCA) was selected as the guest molecule for the PEG-b-PCD host, since the inclusion interaction of adamantyl group with β-CD is strong. For the preparation of polyion complex (PIC) like assemblies, PEG-b-PCD and ADCA (2 fold in excess of that of β-CD group) were co-dissolved in 0.05 M NaOH aqueous solution, which was dialyzed (MWCO: 6-8 kDa) against deionized water for 1 day and then lyophilized. The dried product (8.0 mg) was dissolved in deionized water (4.0 ml), into which 5.0 mg PEI in 1.0 ml water was added dropwise under sonication. The solution was subjected to dialysis against deionized water for 1 day. The dialysate was filtered through a 0.22 μm syringe filter.

A pseudo-polyelectrolyte copolymer with one negatively charged block was prepared by taking advantage of the host-guest interaction between PEG-b-PCD and ADCA, further electrostatic interaction of this supramolecular polyelectrolyte and polyethylenimine (PEI) led to the formation of PIC-like assemblies with polyelectrolyte complex cores comprised of PEI and ADCA included block containing β-CD.

PEG-b-PCD/ADCA Host/Guest Assemblies

Figure 26:
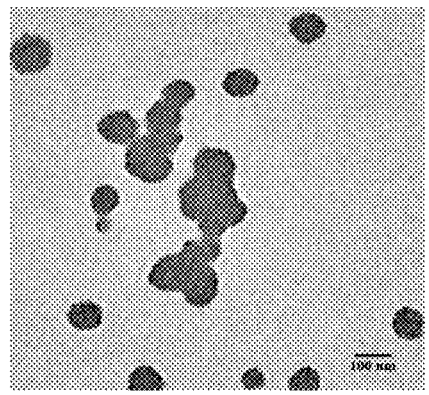
FIG. 26 is a TEM image of PEG-b-PCD assemblies containing ADAC and PEI.
Figure 27:
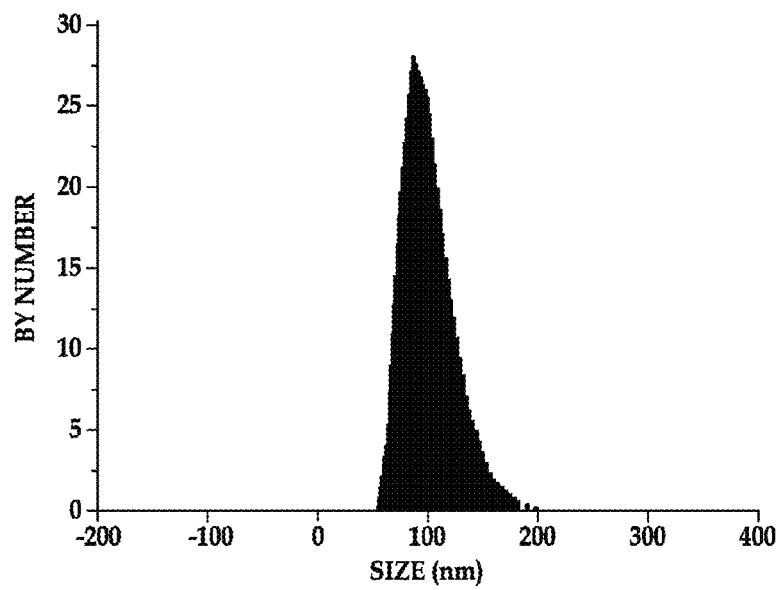
FIG. 27 is a particle size distribution graph of PEG-b-PCD assemblies containing ADAC and PEI.

TEM observation indicated that these assemblies displayed nearly spherical morphology with a mean size of 100.7 nm (FIG. 26). The mean number-average diameter determined by DLS was 97.1 nm (FIG. 27). These results suggest that copolymers with architecture like PEG-b-PCD are suitable for use as a delivery vector for water-soluble bioactive macromolecules including peptides, proteins, therapeutic DNAs and small interfering RNAs.

Example 4

PEI-CD-PEG Assemblies with a Hydrophobic Drug

In this example, the assemblies include a cyclodextrin containing graft copolymer based on branched polyethyleneimine formulated via the scheme shown in FIG. 3.

Synthesis of PEI-CD-PEG (Also Referred to Herein as PEI-25 kDa-CD-PEG)

1.0 g of branched PEI (Mw=25 kDa) was dissolved in 10 ml DMSO, into which 10 ml DMSO containing 2.0 g mono-6-(p-tosyl)-β-CD was added. The reaction was performed at 75° C. for 7 days, and then the polymer was purified by dialysis. Polyethylene glycol (PEG) was covalently linked to the CD conjugated PEI by reacting polyethylene glycol methacrylate (Mn=526 Da, Sigma) with PEI-CD. The resulting copolymer was purified by dialysis.

Figure 28:
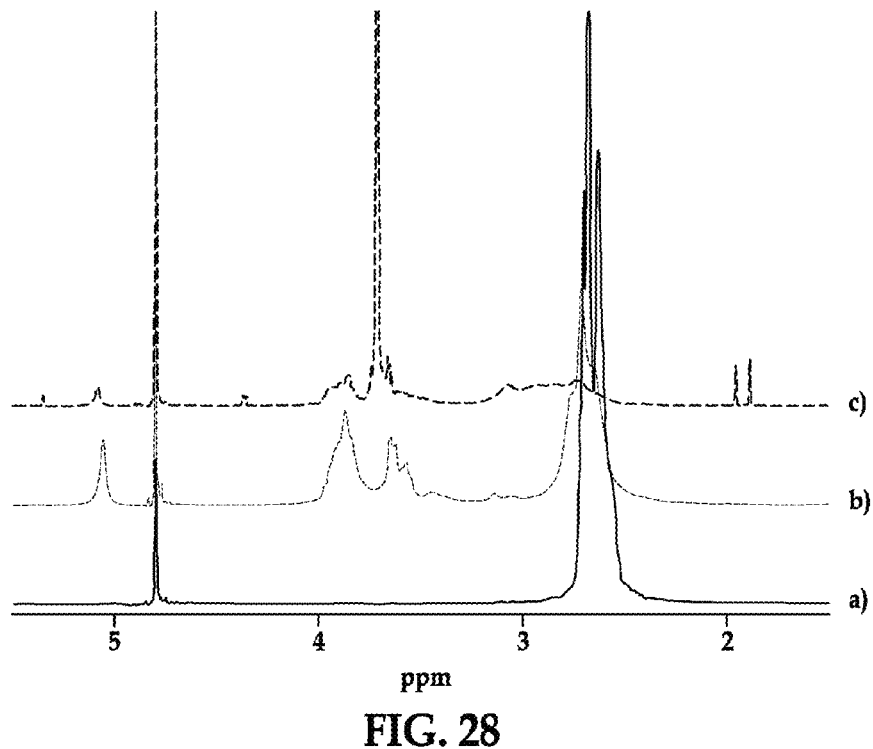
FIG. 28 illustrates the $^1$H NMR spectra of PEI-25 kDa and its derivatives: a) PEI-25 kDa, b) PEI-25 kDa-CD, and c) PEI-25 kDa-CD-PEG.
Figure 29:
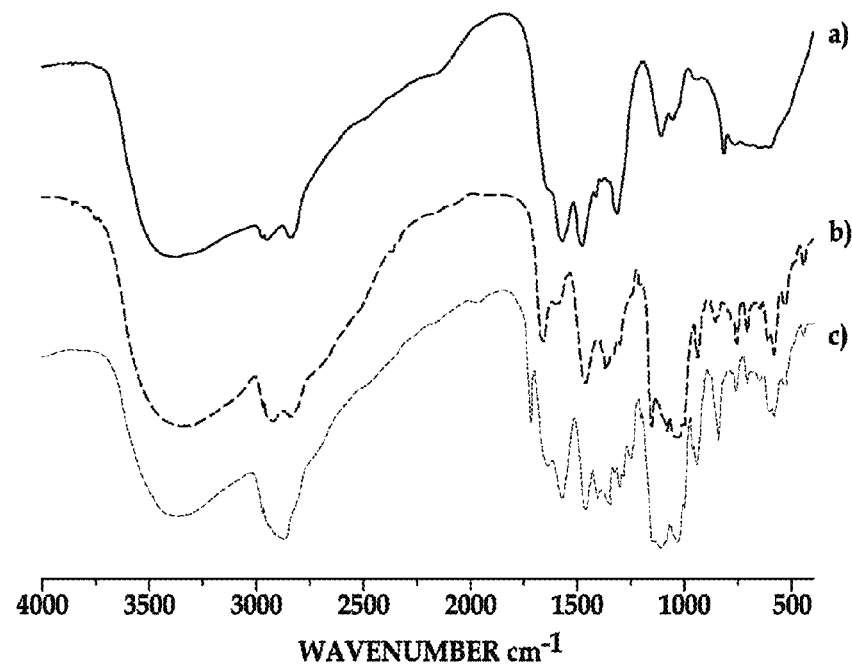
FIG. 29 illustrates the FT-IR spectra of PEI-25 kDa and its derivatives: a) PEI-25 kDa, b) PEI-25 kDa-CD, and c) PEI-25 kDa-CD-PEG'.

$^1$H NMR and FT-IR were adopted to characterize the copolymer. As shown in FIG. 28, the proton signals at 3.4-4.0 ppm and 5.1 ppm (which are characteristic signals of β-CD) suggested the successful conjugation of β-CD. On the other hand, the significant enhancement of the signal at 3.7 ppm indicated the introduction of PEG chains. Still further, the $^1$H NMR measurement suggested that CD conjugated PEI (PEI-CD) with an ethylene/CD ratio of 21.6 was obtained. This result was consistent with the FT-IR measurements illustrated in FIG. 29, where absorption at 1000 to 1150 cm$^{-1}$ was increased as β-CD and PEG were conjugated onto the side chains of PEI. These result suggested the successful synthesis of hydrophilic copolymer containing β-CD and PEG.

Preparation of PEI-CD-PEG/Indomethacin (IND) Host/Guest Assemblies

Figure 30:
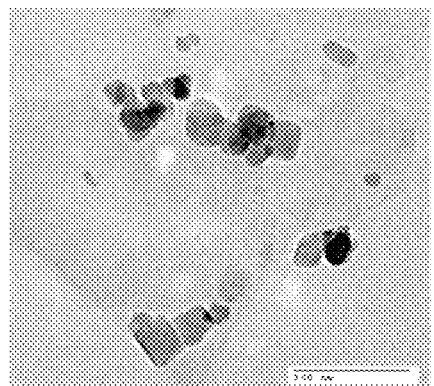
FIG. 30 is a TEM image of assemblies based on PEI-CD-PEG in the presence of indomethacin.

To prepare the assemblies, indomethacin (IND), a hydrophobic non-steroidal anti-inflammatory drug, was used with the PEI-CD-PEG. Via dialysis method, IND-containing assemblies were prepared. Mixtures of IND and the copolymer with a certain weight ratio were co-dissolved in dimethylsulfoxide (DMSO) at 50° C. with a final polymer concentration of 10 mg/ml. This solution was placed into a dialysis tubing (MWCO 6-8 kDa) for dialysis against deionized water for 24 hours at 25° C. The outer aqueous solution was renewed every 30 min for the first 2 hours, and then every 2 hours for the remaining period of time. The dialysis solution was filtered through a 0.45 μm syringe filter. FIG. 30 illustrates that nanoparticles with a diameter of about 30 nm were prepared.

Example 5

PEG-b-PLL(CD) Assemblies with a Hydrophobic Polymer

In this example, the assemblies include a copolymer based on polyethylene glycol-block-poly(L-lysine) having cyclodextrin units conjugated thereto during a nucleophilic reaction.

Synthesis of PEG-b-PLL(CD) (Also Referred to Herein as PEG-Plys-CD)

ε-(benzyloxycarbonyl)-L-lysine (Lys(Z)-NCA) was polymerized in DMF at 40° C. by the initiation from the terminal primary amino group of MPEG-NH$_2$ to obtain PEG-b-P(Lys (Z)). The copolymer polyethylene glycol-block-poly(L-lysine) (PEG-b-PLL) was obtained by the de-protection of PEG-b-P(Lys(Z)) in trifluoroacetic acid.

PEG-b-PLL(CD) was synthesized by nucleophilic reaction. Lyophilized PEG-b-PLL was reacted with 5 fold excess amount of 6-monotosyl β-CD in anhydrous DMSO. After 5 days of reaction, the mixture was dialyzed against 0.1 N NaOH for 2 days to remove unreacted 6-monotosyl β-CD, and then was dialyzed against distilled water for 2 days. After it was filtered through a 0.22 μm syringe filter, the resultant aqueous solution was lyophilized to obtain a brown powder.

Figure 31:
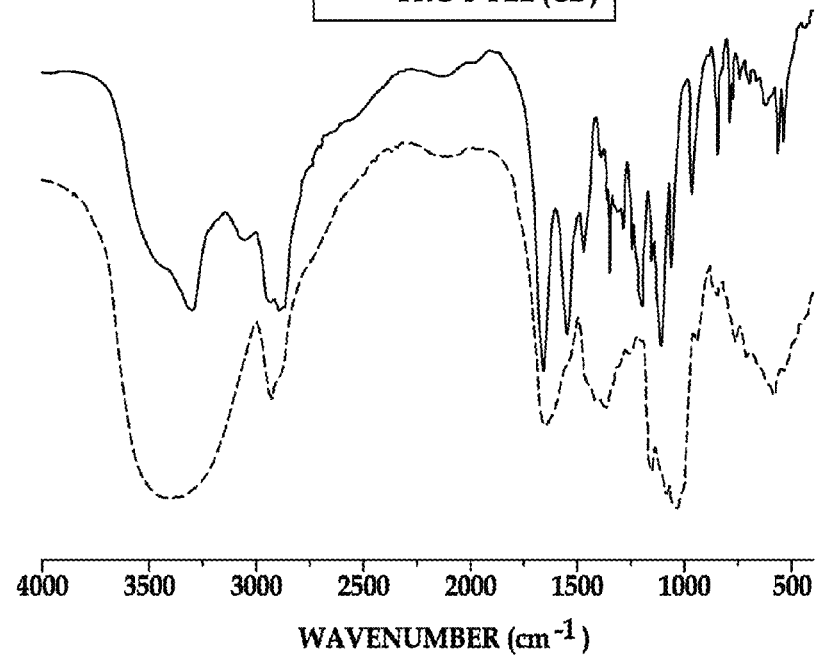
FIG. 31 illustrates the FT-IR spectra of PEG-b-PLL and PEG-b-PLL(CD)
Figure 32:
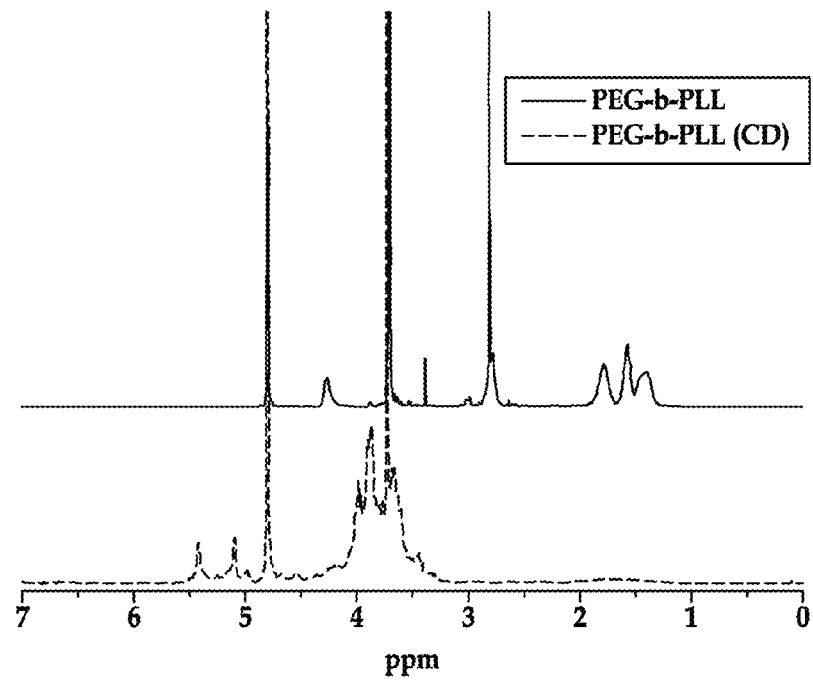
FIG. 32 illustrates the $^1$H NMR spectra of PEG-b-PLL and PEG-b-PLL(CD)
Figure 33A:
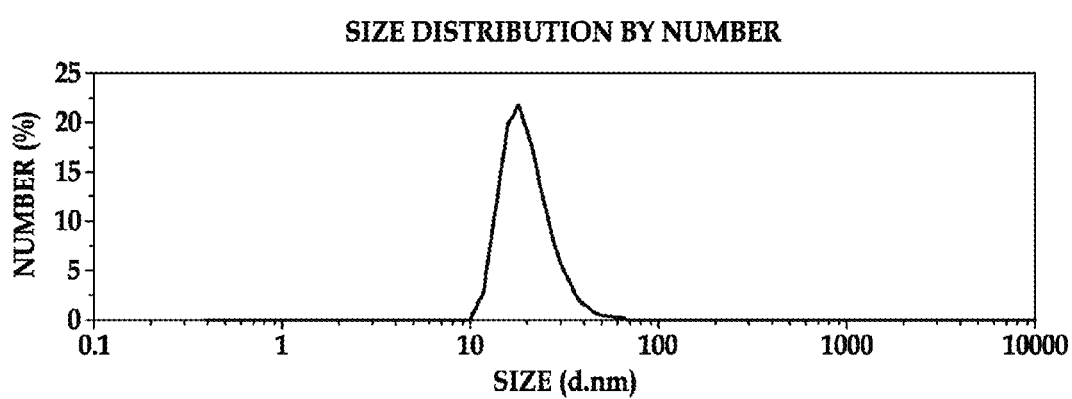
FIGS. 33A-33D illustrate the effect of PEG-b-PLL(CD)/PBLA ratio on the particle size of assemblies.
Figure 33B:
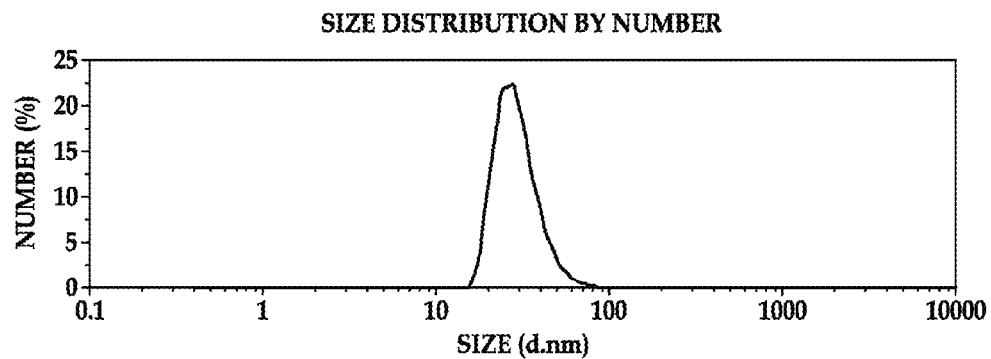
Figure 33C:
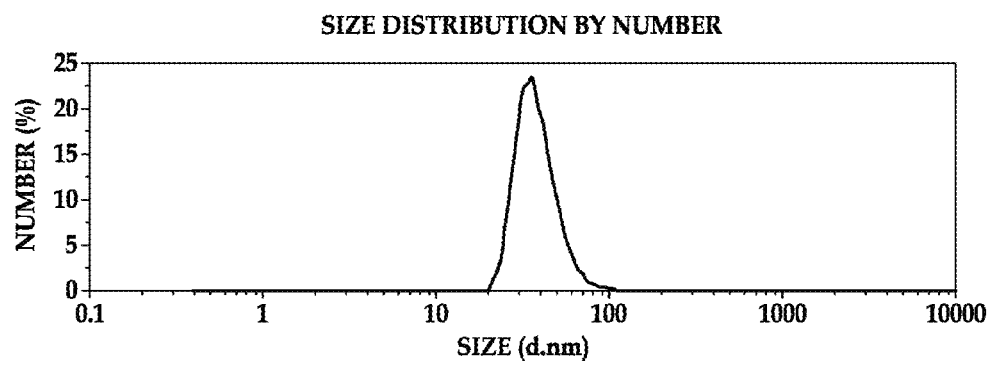
Figure 33D:
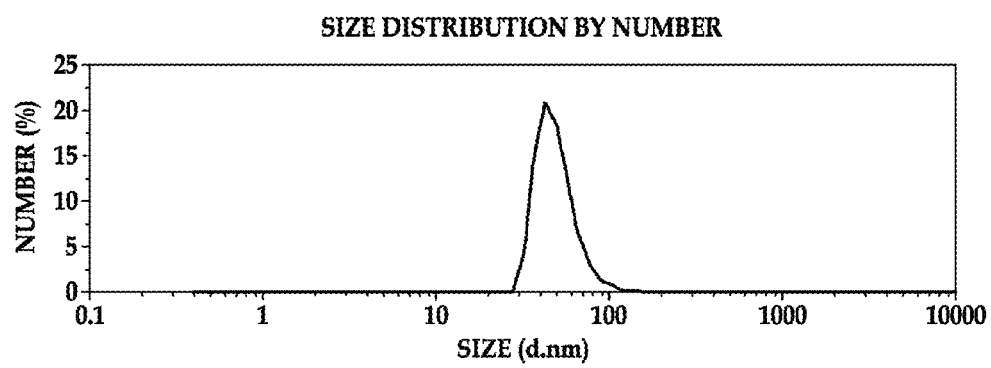
Figure 34A:
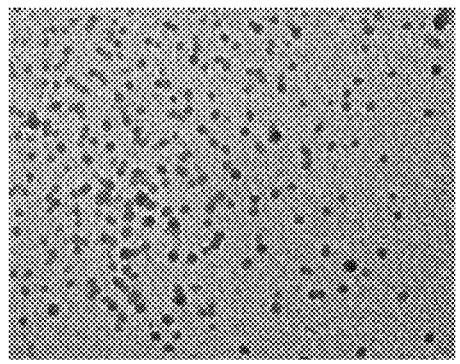
FIGS. 34A and 34B are TEM images of assemblies based on PEG-b-PLL(CD):PBLA at a ratio of 10:2 (FIG. 34A) and at a ratio of 10:4 (FIG. 34B)
Figure 34B:
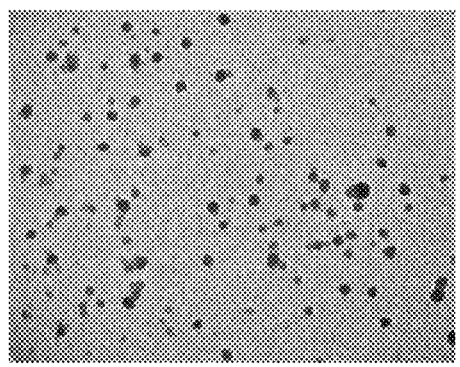
Figure 35A:
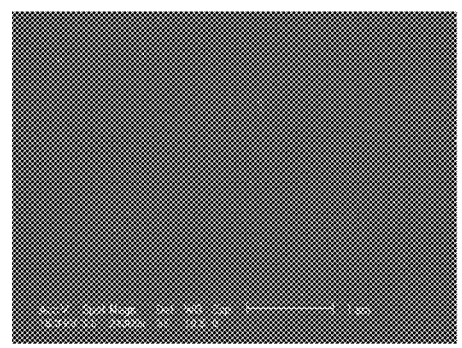
FIGS. 35A and 35B are SEM (scanning electron microscopy) images of assemblies based on PEG-b-PLL(CD): PBLA at a ratio of 10:2 (FIG. 35A) and at a ratio of 10:4 (FIG. 35B).
Figure 35B:
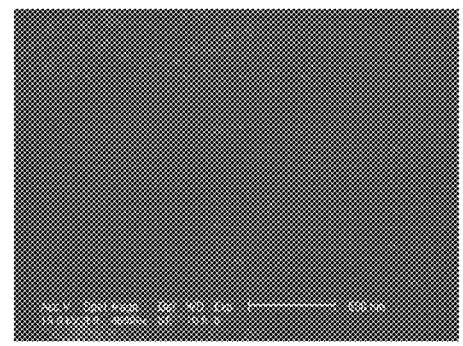

FT-IR spectra shown in FIG. 31 and $^1$H NMR spectra in FIG. 32 indicated the successful introduction of β-CD units onto the side chain of PEG-b-PLL.

Preparation of PEG-b-PLL(CD)/PBLA Host/Guest Assemblies

Assemblies based on PEG-b-PLL(CD) were prepared by dialysis procedure. 10 mg PEG-b-PLL(CD) was dissolved into 1.0 ml deionized water. Into this solution, 1.0 ml DMSO solution containing different amounts of PBLA was added with sonication. The mixture solution obtained was dialyzed (MWCO: 7-8 kDa) against deionized water for 24 hours. Physicochemical characterization was performed after the aqueous solution was filtered through a 0.8 μm syringe filter.

FIGS. 33A through 33D show the particle size of assemblies based on PEG-b-PLL(CD)/PBLA of different weight ratios. The average size (by number) increased as PBLA content increased. The mean size was 30, 41, 52, and 66 nm for assemblies based on formulations with PEG-b-PLL(CD)/PBLA ratio of 10:0.5, 10:1, 10:2 and 10:4 respectively.

As shown in FIGS. 34A, 34B, 35A and 35B, the morphology based on TEM and SEM images suggested that these assemblies exhibited a spherical shape independent of preparation formulation.

The solubilization effect of cyclodextrins (α, β or γ) to a broad range of hydrophobic compounds has advantageously been utilized to develop the water soluble copolymers disclosed herein. As previously described hereinabove, the copolymers include the cyclodextrin hydrophilic segment and another stabilizing hydrophilic segment (that does not include cyclodextrins), which enables the copolymers to form assemblies for use as versatile carriers.

While several embodiments have been described in detail, it will be apparent to those skilled in the art that the disclosed embodiments may be modified. Therefore, the foregoing description is to be considered exemplary rather than limiting.

What is claimed is:

1. A water soluble copolymer, comprising:
   a first hydrophilic block segment or graft chain that contains cyclodextrin groups in at least a majority of its repeating units; and
   a second hydrophilic block segment or graft chain covalently linked to the first hydrophilic block segment or graft chain, the second hydrophilic block segment or graft chain containing repeating units other than cyclodextrin groups;
   the second hydrophilic block segment or graft chain being a polyethylene glycol block segment;
   wherein a block segment or graft chain of the first hydrophilic block segment or graft chain is different from the second hydrophilic block segment or graft chain;

and wherein the first hydrophilic block segment is a polyaspartamide block carrying α-cyclodextrin groups, β-cyclodextrin groups or γ-cyclodextrin groups;
the water soluble copolymer having the structure:

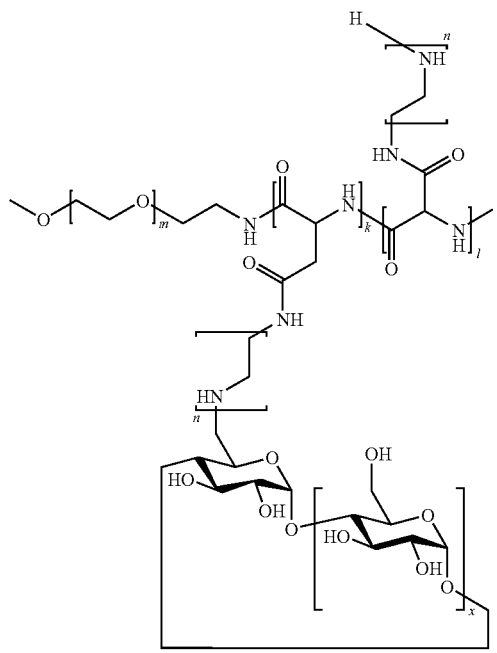

wherein m=5 to 500, wherein n=1 to 5, wherein k+l=5 to 100 and k≧1>0, and wherein X=5 when the first hydrophilic block segment is the polyaspartamide block carrying α-cyclodextrin groups, X=6 when the first hydrophilic block segment is the polyaspartamide block carrying β-cyclodextrin groups, or X=7 when the first hydrophilic block segment is the polyaspartamide block carrying γ-cyclodextrin groups.

2. An assembly, comprising:
a hydrophobic core including:
the first hydrophilic block segment of the water soluble copolymer of claim 1; and
at least one hydrophobic guest molecule or polymer that is inserted or partially inserted in the cyclodextrin units to hydrophobilize the first hydrophilic block segment; and
a hydrophilic shell including the second hydrophilic block segment of the water soluble copolymer of claim 1.

3. The assembly as defined in claim 2 wherein the assembly is a nanoparticle or a microparticle.

4. The assembly as defined in claim 2 wherein the at least one hydrophobic guest molecule or polymer is selected from pyrene, coumarin 102, rapamycin, dexamethasone, indomethacin, ibuprofen, adamantine-carboxylic acid, poly(β-benzyl L-aspartate), polystyrene, or poly(D,L-lactide).

* * * * *